United States Patent
Rahimi et al.

(10) Patent No.: US 12,208,012 B2
(45) Date of Patent: Jan. 28, 2025

(54) SYSTEM AND METHODS FOR LASER-ASSISTED NANOTEXTURING AND SILVER IMMOBILIZATION ON TITANIUM IMPLANT SURFACES

(71) Applicant: Purdue Research Foundation, West Lafayette, IN (US)

(72) Inventors: Rahim Rahimi, West Lafayette, IN (US); Vidhya Selvamani, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 14 days.

(21) Appl. No.: 18/092,267

(22) Filed: Dec. 31, 2022

(65) Prior Publication Data

US 2023/0270555 A1 Aug. 31, 2023

Related U.S. Application Data

(60) Provisional application No. 63/314,123, filed on Feb. 25, 2022.

(51) Int. Cl.
*A61F 2/30* (2006.01)

(52) U.S. Cl.
CPC .. *A61F 2/3094* (2013.01); *A61F 2002/30784* (2013.01); *A61F 2002/3084* (2013.01); *A61F 2002/3097* (2013.01); *A61F 2310/00023* (2013.01); *A61F 2310/0052* (2013.01)

(58) Field of Classification Search
CPC .......... A61F 2/30767; A61F 2310/0052; A61F 2310/00023; A61F 2002/3097; A61F 2/309; A61L 27/06

USPC .............................. 623/23.374, 23.5; 427/2.1
See application file for complete search history.

(56) References Cited

FOREIGN PATENT DOCUMENTS

| CN | 1772949 | * | 5/2006 |
| CN | 107233618 | * | 10/2017 |

OTHER PUBLICATIONS

Trampuz, A. et al., Molecular and Antibiofilm Approaches to Prosthetic Joint Infection. Clinical Orthopaedics and Related Research, 2003, vol. 414; pp. 69-88.
Gristina, A. G. et al., Infections From Biomaterials and Implants: A Race for the Surface. Medical Progress through Technology, 1988, vol. 14; pp. 205-224.
Narenkumar, J. et al., Effect of crude methanolic extract of Lawsonia inermis for anti-biofilm on mild steel 1010 and its effect on corrosion in a re-circulating wastewater system. Journal of King Saud University—Science, 2021, vol. 33, No. 8, 101611; 7 pgs.; available online Sep. 21, 2021.

(Continued)

*Primary Examiner* — Tabassom Tadayyon Eslami
(74) *Attorney, Agent, or Firm* — Purdue Research Foundation

(57) ABSTRACT

A method for manufacturing an implantable device is provided. The method includes laser nano-texturing a titanium surface. The method further includes applying an aqueous silver ion solution to form a silver ion complex on the nano-textured titanium surface. The method also includes reducing, using laser-assisted photocatalytic reduction, the silver ion complex to silver ion particles which are immobilized on the nano-textured titanium surface.

7 Claims, 17 Drawing Sheets

(56) References Cited

OTHER PUBLICATIONS

Li, Y. et al., Near-Infrared Light Triggered Phototherapy and Immunotherapy for Elimination of Methicillin-Resistant *Staphylococcus aureus* Biofilm Infection on Bone Implant. ACS Nano, 2020, vol. 14, No. 7, pp. 8157-8170; published Jun. 25, 2020.

Su, K. et al., Rapid Photo-Sonotherapy for Clinical Treatment of Bacterial Infected Bone Implants by Creating Oxygen Deficiency Using Sulfur Doping. ACS Nano, 2020, vol. 14, No. 2, pp. 2077-2089; published Jan. 28, 2020.

Feng, L. et al., Super-Hydrophobic Surfaces: From Natural to Artificial. Advanced Materials, 2002, vol. 14, No. 24, pp. 1857-1860.

Serrano, C. et al., Nanostructured medical sutures with antibacterial properties. Biomaterials, 2015, vol. 52, pp. 291-300; published online Feb. 28, 2015.

Han, S. et al., Efficacy of antifreeze proteins from Clupea harangues and Anarhichas minor on gas hydrate inhibition via cell surface display. Chemical Engineering Science, 2020, vol. 215, 115470; 12 pgs.

Zhang, Y. et al., Nano Ag/ZnO-Incorporated Hydroxyapatite Composite Coatings: Highly Effective Infection Prevention and Excellent Osteointegration. ACS Applied Materials & Interfaces, 2018, vol. 10, No. 1, pp. 1266-1277; published Dec. 11, 2017.

Fuchs, T. et al., The use of gentamicin-coated nails in the tibia: preliminary results of a prospective study. Archives of Orthopaedic and Trauma Surgery, 2011, vol. 131, No. 10, pp. 1419-1425; published online May 24, 2011.

Atiyeh, B. S. et al., Effect of silver on burn wound infection control and healing: Review of the literature. Burns, 2007, vol. 33, No. 2, pp. 139-148.

Nejati, S. et al., Laser Functionalization of Carbon Membranes for Effective Immobilization of Antimicrobial Silver Nanoparticles. Journal of Environmental Chemical Engineering, 2020, vol. 8, No. 5, 104109; 9 pgs.

Maruthamuthu, M. k. et al., Construction of a high efficiency copper adsorption bacterial system via peptide display and its application on copper dye polluted wastewater. Bioprocess and Biosystems Engineering, 2015, vol. 38, No. 11, pp. 2077-2084; published online Jul. 29, 2015.

Zareei, A. et al., Highly Conductive Copper-Silver Bimodal Paste for Low-Cost Printed Electronics. ACS Applied Electronic Materials, 2021, vol. 3, No. 8, pp. 3352-3364; published Aug. 13, 2021.

Selvi, A. et al., Characterization of biospheric bacterial community on reduction and removal of chromium from tannery contaminated soil using an integrated approach of bio-enhanced electrokinetic remediation. Journal of Environmental Chemical Engineering, 2021, vol. 9, No. 6, 106602, 9 pgs; available online Oct. 22, 2021.

Ahmed, A. R. et al., Reduction in burst release after coating poly (D, L-lactide-co-glycolide)(PLGA) microparticles with a drug-free PLGA layer. Pharmaceutical Development and Technology, 2012, vol. 17, No. 1, pp. 66-72.

Wu, J. et al., Responsive Assembly of Silver Nanoclusters with a Biofilm Locally Amplified Bactericidal Effect to Enhance Treatments against Multi-Drug-Resistant Bacterial Infections. ACS Central Science, 2019, vol. 5, No. 8, pp. 1366-1376; published Jun. 18, 2019.

Lu, T. et al., Surface modification of biomaterials using plasma immersion ion implantation and deposition. Interface Focus, 2012, vol. 2, No. 3, pp. 325-336; published online Mar. 21, 2012.

Green, J.-B. D. et al., Review of immobilized antimicrobial agents and methods for testing. Biointerphases, Dec. 2011, vol. 6, No. 4, pp. MR13-MR28; published Oct. 24, 2011.

Herbani, Y. et al., Silver nanoparticle formation by femtosecond laser induced reduction of ammonia-containing AgNO3 solution, 2nd International Symposium on Frontier of Applied Physics (ISFAP 2016), IOP Conference Series: Journal of Physics: Conference Series, 2017, vol. 817, 021048; 6 pgs.

Faria, D. et al., Laser-assisted production of HAp-coated zirconia structured surfaces for biomedical applications. Journal of the Mechanical Behavior of Biomedical Materials, 2020, vol. 112, 104049, 14 pgs; available online Aug. 26, 2020.

Miranda, G. et al., Surface design using laser technology for Ti6Al4V-hydroxyapatite implants. Optics and Laser Technology, 2019, vol. 109, pp. 488-495; available online Aug. 28, 2018.

González-Castillo, J.R. et al., Synthesis of Ag@Silica Nanoparticles by Assisted Laser Ablation. Nanoscale Research Letters, Nano Express, 2015, vol. 10, No. 1, p. 399 (9 p. ); published online Oct. 13, 2015.

Li, J. et al., Microstructure and properties of Ag/N dual ions implanted titanium. Surface and Coatings Technology 2011, 205 (23-24), 5430-5436.

Li, M. et al., Highly effective and noninvasive near-infrared eradication of a *Staphylococcus aureus* biofilm on implants by a photoresponsive coating within 20 min. Advanced Science 2019, 6 (17), 1900599.

Zwahr, C. et al., Fabrication of multifunctional titanium surfaces by producing hierarchical surface patterns using laser based ablation methods. Scientific reports 2019, 9 (1), 1-13.

Ulerich, J. P. I. et al., Modifications of Ti—6Al—4V surfaces by direct-write laser machining of linear grooves, Photon Processing in Microelectronics and Photonics VI, International Society for Optics and Photonics: 2007; p. 645819.

Sedaghat, S. et al., Laser-Induced Mesoporous Nickel Oxide as a Highly Sensitive Nonenzymatic Glucose Sensor. ACS Applied Nano Materials 2020, 3 (6), 5260-5270.

Sedaghat, S. et al., Laser-induced atmospheric CuxO formation on copper surface with enhanced electrochemical performance for non-enzymatic glucose sensing. Journal of Materials Chemistry C 2021, 9 (42), 14997-15010.

Rahimi, R. et al., Direct Laser Writing of Porous-Carbon/Silver Nanocomposite for Flexible Electronics. ACS applied materials & interfaces 2016, 8 (26), 16907-16913.

Babuska, V. et al., Proliferation of osteoblasts on laser-modified nanostructured titanium surfaces. Materials 2018, 11 (10), 1827.

Babuska, V. et al., Repeated exposure of nanostructured titanium to osteoblasts with respect to peri-implantitis. Materials 2020, 13 (3), 697.

Roth, A. et al., Wearable and Flexible Ozone Generating System for Treatment of Infected Dermal Wounds. Frontiers in Bioengineering and Biotechnology 2020, 8.

Davidson, J. L. et al., A paper-based colorimetric molecular test for SARS-CoV-2 in saliva. Biosensors and Bioelectronics: X 2021, 9, 100076.

\* cited by examiner

SYSTEM AND METHODS FOR LASER-ASSISTED NANOTEXTURING AND SILVER IMMOBILIZATION ON TITANIUM IMPLANT SURFACES

CROSS REFERENCE TO RELATED APPLICATIONS

This application claims the benefit of U.S. Provisional Application No. 63/314,123 filed Feb. 25, 2022 and is incorporated by reference herein in its entirety.

TECHNICAL FIELD

This disclosure relates to implantable device and, in particular, to antimicrobial enhancements for implantable devices.

BACKGROUND

Orthopedic implants are expected to restore function in load-bearing joints and should be able to sustain a high level of mechanical stress, wear, and fatigue. According to the American Joint Replacement Registry, 860,000 total hip and knee arthroplasties were performed in 2016 alone. Despite many improvements in surgical practices, orthopedic and trauma device-related infection (ODRI) remains a major complication in orthopedic surgeries and occurs in 7% of the cases[3]. Among different materials, Titanium (Ti) and its alloys are the most popular materials that are commonly used in the orthopedic field due to their reliable mechanical performance and as a replacement for hard bone tissues. Because of its bio-inert nature, pristine Ti surfaces are vulnerable to bacterial adhesion and biofilm formation, which can cause ODRI after surgery.

BRIEF DESCRIPTION OF THE DRAWINGS

The embodiments may be better understood with reference to the following drawings and description. The components in the figures are not necessarily to scale. Moreover, in the figures, like-referenced numerals designate corresponding parts throughout the different views.

DETAILED DESCRIPTION

Figure 1:
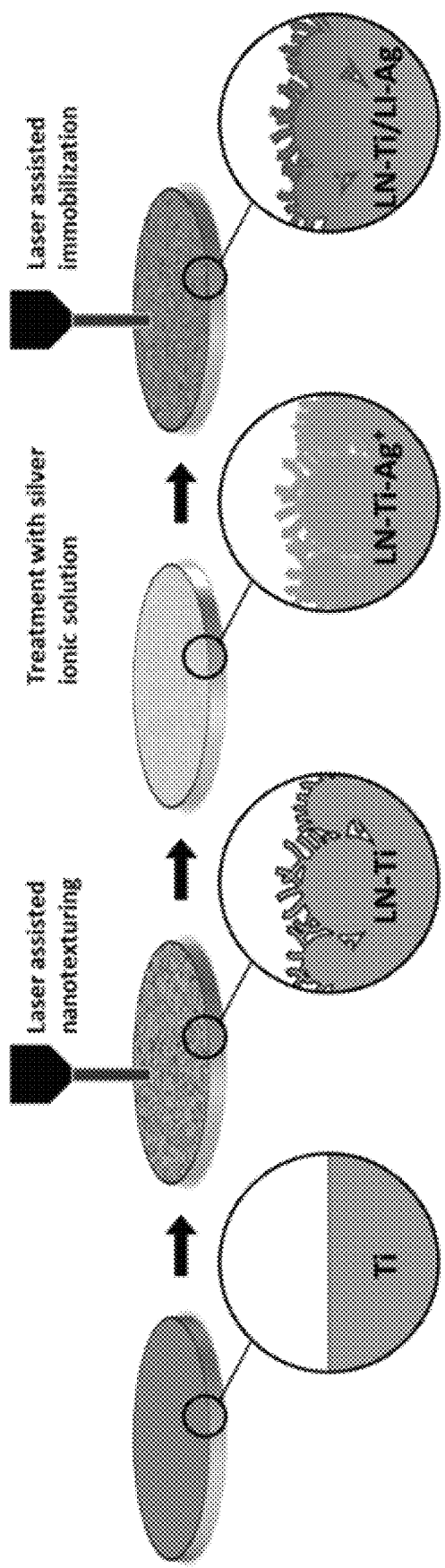
FIG. 1 illustrates a process showing laser-assisted nanotexturing and silver immobilization on titanium implants for enhanced osseointegration and antimicrobial properties.

Once biofilm has formed on a surface of an implant, it is extremely difficult to treat the infection even with a large dose of antibiotics. In general, implant-related infections can be explained by the "race for surface" concept, where there is a competition between the host cells and bacteria to attach to the implant surface and proliferate. Prompt and rapid integration of host cells with implant surface is key to prevent bacterial adhesion onto the implant surface. As such, various surface modification methods of Ti implants have been used to produce the desired surface roughness and topography onto implant surfaces which can be widely classified into chemical and physical. Some of the examples of the chemical process include chemical etching, electrodeposition, lithography, and anodization physical (subtractive) processes include milling, grit-blasting, and laser texturing. These techniques augment the surface roughness of the metal implant by controlled addition or removal of material. However, each process has its own disadvantages. For instance, the chemical process involves multiple steps and the utilization of toxic chemicals with subsequent accumulation of hazardous waste. In short, chemical processes are slow and limited to create nanoscale roughness. While physical processes are often limited to create large micronscale roughness on the implant surface and incapable of modifying the chemical composition, and surface energy (wettability) of the implant surface. Surface characteristics of Ti implants such as topography (macro-, micro- and nano-scale), surface chemistry, surface energy or wettability, and charge are inter-related properties and cooperatively influence cellular integration onto implant material. For example, macro- and micrometer roughness facilitate fibroblast cells adhesion and mechanical anchorage to bone. Nanometer surface roughness shows enhanced protein adsorption and adhesion of osteoblastic cells on the implant surfaces. Furthermore, studies have shown that hydrophilic surfaces show enhanced bone cell adhesion, proliferation and differentiation. Therefore, an ideal Ti implant surface would have a hierarchal micro and nano roughness with stable hydrophilic properties that will promote the overall process of osseointegration and stable mechanical anchorage to the bone.

Among the different aforementioned surface micromachining tools, laser-assisted nano texturing (LN) provides the unique ability to selectively modify both the physical and chemical properties of metal surfaces. A laser beam modifies the surface of a material by locally heating and vaporizing portions of the workpiece in a controlled manner with the formation of hierarchical micro/nano structures. The created surface topography is highly dependent on the laser processing power and scanning speed. Besides, the environment in which laser processing is conducted has a great influence on the chemical composition of the processed surface. Laser irradiation of metals and alloys in normal air or controlled oxygen-rich atmosphere leads to the formation of surface metal oxides with highly stable hydrophilic properties. Other advantages of LN are processing speed, easy automation, and the possibility to treat large areas.

Due to such advantages, LN has been used to enhance the biological response such as cellular integration, protein adsorption of a wide range of implantable devices of various geometries made with Ti, Ti-based alloys. It is also important to point out that while such nano-textured and hydrophilic surfaces can improve the rate of host cell attachment, they also provide an attractive surface for rapid and stronger attachment of bacteria and biofilm formation. If the bacterial attachment occurs before tissue regeneration, it is often impossible for the host defense to eliminate the bacteria and prevent biofilm formation. Therefore, an ideal implant surface must accelerate and improve the host-cell attachment and have antibacterial properties to prevent bio substances and bacteria from adhering onto its surface.

A common strategy to prevent implant-associated infection involves coating the implant with an anti-biofouling coating such as anti-adhesive inert polymers, the main disadvantage of these surfaces is it repels bacteria rather than killing it. Other coatings with bacterial killing capabilities are photo-responsive coatings, antimicrobial peptides, drugs, metallic nanoparticles with bactericidal properties (e.g., silver (Ag), copper (Cu), Chromium (Cr) and Sulfur (S)). The most used antibacterial coating is the application of antibiotics such as penicillin, ceftriaxone, levofloxacin, erythromycin, and tetracycline on implant surfaces. However, long-term antibacterial protection is not possible with these drug coatings as a large portion of the loaded drug is released in a short time (burst release). In addition, there is often a mixture of microbes that are found in implant-associated infection; hence it is essential to choose a bactericidal agent with a broad spectrum. Functional metallic nanoparticles serve as more effective bactericidal coating on implantable devices as they offer good stability, broad antibacterial spectrum, strong oligodynamic effect, and low incidence of antibiotic resistance.

Among different chemicals, the bactericidal properties of $Ag^+$ and Ag nanoparticles (AgNPs) are well documented in the previous studies. Hence, various surface modification techniques for AgNP coating onto implants surface have been developed to obtain antibacterial properties. Nonetheless, AgNPs at high concentration can be toxic to surrounding host cells and impair healing, and cellular integration. A rational approach to overcome the cytotoxic effect of AgNPs would be to immobilize them on the implant surface. Immobilization of AgNPs is often achieved through chemical reaction on the implant surface such as sol-gel, silanization and layer-by-layer self-assembly as well as in situ synthesis. However, in many such chemical processes the nanoparticles are immobilized onto the implant surface through weak electrostatic interactions which lack the mechanical robustness that is required for orthopedic application.

Laser immobilization (LI) can be considered as an alternative for the existing in situ AgNPs synthesis and immobilization procedures. The photo and thermal energy of the laser beam has the ability to reduce and immobilize many silver ionic compounds to metallic nanoparticles directly onto target metallic surfaces. In addition, this technique provides a green synthesis of AgNPs as it eliminates the requirement of any kind of chemical reducers and stabilizers in its process. Therefore, the system and methods described herein explore and provide the use of an all laser-based approach to both create a hierarchical nanostructure and immobilize AgNPs directly onto Ti implant surfaces to effectively increase both osseointegration and antimicrobial properties.

The system and methods described herein provide a facile approach for manufacturing implants with antimicrobial properties and enhanced cellular mineralization properties. Nanotexturing may be performed on implant grade Ti surfaces using a nanosecond laser irradiation which provides the fabrication of hierarchical structures. Subsequently, nanotextured surfaces were immobilized with Ag nanoparticles by the second laser treatment. This immobilization step limited the leaching of AgNPs into the environment. Through various experimentation and validation, the laser-treated surfaces are found to have enhanced bone cell mineralization and bactericidal properties. These steps may be completed in an ambient environment making the process scalable and cost-effective. Improved cellular mineralization and robust antibacterial property are a step forward in reducing post-operative infections in orthopedic surgeries.

The systems and methods described herein offer improvements over existing market solutions. Additional benefits, efficiencies, and improvements over existing market solutions are made evident in the systems and methods described herein.

FIG. 1 illustrates a process showing laser-assisted nano-texturing and silver immobilization on titanium implants for enhanced osseointegration and antimicrobial properties. The process may be described, according to various embodiments as laser nano-texturing a titanium surface of a medical device that will be fully or partially disposed in the body. Then, applying an aqueous silver ion solution to form a silver ion complex on the laser nano-textured titanium (LN-Ti) surface. Then, reducing, using laser-assisted photocatalytic reduction, the silver ion complex to silver ion particles which are immobilized on the nano-textured titanium surface.

Various laser powers (i.e. 8, 16, 24, 32, and 40W) may be selected to establish the optimal laser settings to develop nanotextured surfaces with superior osseointegration properties by systematic cellular mineralization studies. As illustrated in FIG. 1, the identified LN-Ti surface with may be treated with silver diaminohydroxide ($[Ag(NH_3)_2]OH$) (LN—Ti—$Ag^+$) followed by laser processing at a lower power to reduce and immobilize $Ag^+$ ions to AgNPs within the porous LN-Ti nanostructure. In various experimentation, it was observed that the resulting laser nanotextured and silver immobilized (LN-Ti/LI-Ag) surfaces provided better cellular mineralization with limited bacterial growth as compared to pristine Ti surface. The cytocompatibility of LN-Ti/LI-Ag surfaces was tested by 3-(4,5-dimethylthiazol-2-yl)-2,5-diphenyl tetrazolium bromide (MTT) assay. Finally, anti-bacterial properties of LN-Ti/LI-Ag were demonstrated by contact killing tests and live dead assay over the course of several days.

Figure 2:
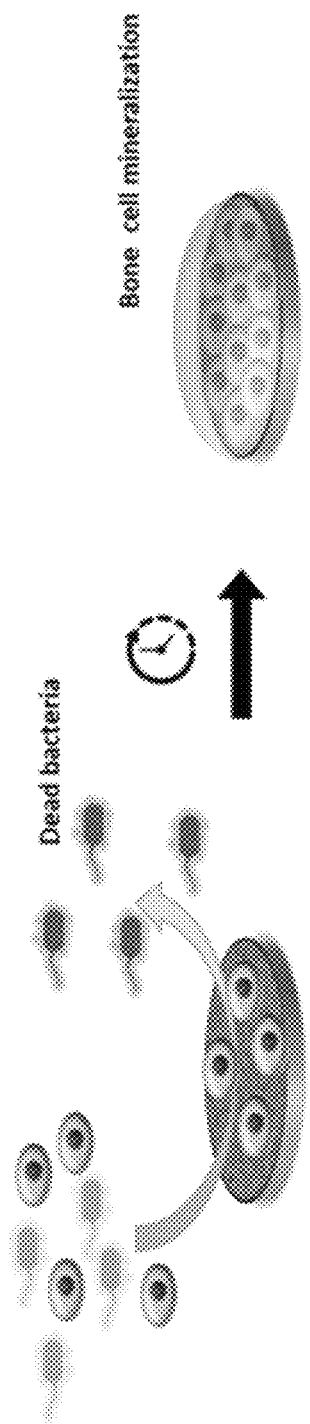
FIG. 2 illustrates an example of a resulting surface that has enhanced bone mineralization and antimicrobial properties.

FIG. 2 illustrates an example of a resulting surface that has enhanced bone mineralization and antimicrobial properties. This illustration shows the competition between bone cells and bacteria for attachment onto the implant surface. The enhanced antibacterial and bone mineralization characteristics of the surface allows a selective attachment of bone cells while eliminating the attachment of the bacteria onto the implant surface.

The enhanced surface may be portion of a medical device that will be placed in a living body. For example, the resultant surface may be placed adjacent to bone. By way of example the medical device may be an orthopedic implant and the surface that receives or is adjacent to existing bone. In other examples, the surface modification can be utilized in many infrastructure use for food and pharmaceutical production lines where surfaces with stable and robust antibacterial properties of the are required.

Various experimentation was performed for examples and embodiments described herein. Discussion related to the experimentation and related results are not intended to be limiting, but to demonstrate the technical advancements disclosed herein.

Experimental Section

Laser nanotexturing and silver immobilization. At first, Ti samples of 12 mm diameter circular disk and 3 mm thickness were cleaned by sonicating in deionized (DI) water for 10 min and dried with a nitrogen gun. The process of LN on Ti sample was performed by a computer-controlled fiber laser cutting and engraving system set at raster mode (PLS6MW, Universal Lasers, Inc., Scottsdale, AZ). The maximum power and speed of the operating laser system were 40 W and 4 m/s, respectively. The used laser beam has a spot size, power, and speed of 50 μm and 1.06 μm, respectively, with pulse duration in the nanosecond range. To fabricate hierarchical structures with a maximum affinity towards mammalian cells, Ti surfaces were LN with a laser beam of varying powers (0, 8, 16, 24, 32, and 40 W) at a scanning speed of 0.4 m/s. The identified LN-Ti surface with micro/nanoporous structures was functionalized with $Ag^+$ ions by dip coating the samples into 1 M silver diaminohydroxide solution ($[Ag(NH_3)_2]OH$) for 10 min in the dark. The silver diaminohydroxide solution was prepared by modified Tollen's process by dissolving 1.69 g of silver nitrate in 6 ml of nano-filtered Deionized (DI) water. Next, ammonium hydroxide was added dropwise, resulting in the formation of brown silver oxide precipitate. The addition was continued until the precipitate was re-dissolved by forming a complex with ammonia. The final volume of the silver diaminohydroxide solution was made up to 10 mL with the addition of the nano-filtered DI water[53]. Ammonium hydroxide was used to stabilize Ag ions and conformably modify the surface chemistry by forming $[Ag(NH_3)_2]^+$ complex on the LN-Ti (which we term as LN—Ti—$Ag^+$)[54]. Functionalized $Ag^+$ ions were reduced and immobilized as AgNPs onto TiO/$TiO_2$ lattices of LN—Ti—$Ag^+$ by LI at a lower laser power of 4 W with a scanning speed of 0.4 m/s (which we term as LN-Ti/LI-Ag). This unique nondestructive laser-induced photoreduction process allows a conformal and strong attachment of Ag onto the Ti surface by simultaneously reducing the Ag ions to elemental Ag and creating metallic Ti—Ag alloy without disrupting the underlying nanostructure of the LN-Ti.

Material characterization. The morphology of Ti samples before and after LN and LI were characterized using a field emission scanning electron microscope (FE-SEM) (Hitachi-S4800) with built-in energy-dispersive X-ray spectroscopy (EDX)[55-56]. Elemental analysis of Ti samples after LN and LI was determined by EDX and gracing angle X-ray diffraction (GIXRD) analysis. The GIXRD experiment was carried out using a PANalytical Empyrean Diffractometer system with a Cu Kα1 (λ=1.5406 Å) source and a constant incident angle of 1°. Surface wetting properties were determined by water contact angle (WCA) measurement (Advanced Goniometer 290f1, ramé-hart Instrument Corporation). In addition, Raman spectroscopy was performed using a micro-Raman system to differentiate between oxides and nano porous Ti-AgNPs alloy tailored by LN and LI. Raman spectra were acquired using a 532 nm laser excitation on a Renishaw InVia Raman spectrometer[57-58]. Mechanical properties of the LN-Ti/LI-Ag were determined by testing the hardness using a Wilson Rockwell Hardness Tester (IL, USA) on the Rockwell Hardness B scale. Ti, Ti treated with silver diaminohydroxide solution (Ti—$Ag^+$), LN-Ti, laser nanotextured Ti treated with silver diaminohydroxide solution (LN—Ti—$Ag^+$), laser nanotextured Ti and immobilized with silver nanoparticles (LN-Ti/LI-Ag) and LN—Ti—$Ag^+$ after polishing (LN—Ti—$Ag^+$-AP) to remove the laser treatment from the surface, and LN-Ti/LI-Ag after polishing (LN-Ti/LI-Ag-AP). The mechanically polished samples were used to assess the possible changes in the mechanical properties of the bulk Ti substrate after the LN-Ti/LI-Ag process. Eight trials were performed across the surface for each sample and the average with one standard deviation was reported. Silver ion ($Ag^+$) leaching study from the surfaces including Ti—$Ag^+$, LN—Ti—$Ag^+$, and LN-Ti/LI-Ag was performed for different incubation times (24, 72, and 144 h) in phosphate-buffered saline (PBS) at 37° C. The concentration of $Ag^+$ present in the leaching solution at different time intervals was monitored by potentiometric titration method using a Silver Ion-Selective Electrode (ISE) in tandem with an auto-titrator system. Further, the remaining content of Ag on the surfaces after each time point was determined by EDX elemental mapping analysis.

Cell mineralization study. In vitro cell mineralization is a common study used to determine the cell adhesion properties of test surfaces as it could be translated into osseointegration property under in vivo conditions[59]. Mesenchymal stem cells (MSCs) (ScienCell) media were used to culture the cells before application to the surface. Gibco DMEM/F-12 media with 10% fetal bovine serum (FBS) and 1% penicillin and streptomycin antibiotics (PenStrep, Thermo Fisher Scientific, Waltham, MA, USA) were used to culture cells on test surfaces. Cells were utilized between passages 3 and 5. Confluence cultured cells were trypsinized and suspended in DMEM/F-12 media with 10% FBS and 1% pen/strep. Cells were counted using a Countess cell counter (Invitrogen). The Ti specimens with different laser processing and Ag surface functionalization conditions were prepared in 1 cm in diameter samples and placed in 24 well tissue culture plates. MSCs suspensions of $50 \times 10^3$ cells/mL were created in 50 ml conical tubs using appropriate growth media. Next, 2 mL of cell suspensions were added onto the samples in 24 well plates giving a cell seeding density of $20 \times 10^3$ cells/$cm^2$. Cells were then placed into a 37° C. humidified incubator. After 24 h, the growth media was exchanged for differentiation media and was changed every 48 h with 1 ml of new media during the first week of culture. During the second and third weeks of culture, differentiation media was changed daily. After 21 days, test samples were fixed with 2% glutaraldehyde solution for 1 h and washed thrice with deionized water. Next, 500 μL of Alizarin red staining (Sigma-Aldrich) solution was added to each well in a 24 well plate containing a sample and allowed to stain for 1 h with rocking agitation. Samples were rinsed 4 times with DI water and allowed to sit overnight in DI water. MSC monolayers formed were removed from samples with tweezers and visualized with an inverted microscope (Nikon Eclipse TS2 Olympus, Waltham, MA) equipped with a monochrome camera (photometric cool snap dyno camera) using NIS-Element's imaging software[60].

To quantify the cell mineralization percentage on each surface, monolayers recovered from respective samples were placed into 1.5 mL microcentrifuge tubes with 200 µL of 2 M hydrochloric acid and allowed to de-stain at 85° C. for 2 h in a heat block. Monolayer debris was centrifuged to the bottom of the tubes at 20,000 RPM for 10 min. Monolayer de-stain containing the solubilized Alizarin Red was used for the quantitative assay. Next, 150 µL of monolayer de-stain was placed into wells of a 96 well plate for each sample and were neutralized with 60 µL of a 6 M sodium hydroxide solution. The absorbance of the samples was read in a spectrophotometer (Versa Max, Molecular Devices) at 405 nm immediately after neutralization to quantify alizarin red staining. Finally, the influence of $Ag^+$ and LI AgNPs on mineralization percentage was quantified by following the above steps on different test surfaces including Ti, Ti—$Ag^+$, LN-Ti, LN—Ti—$Ag^+$, and LN-Ti/LI-Ag. The mineralization percentage on each surface was calculated by $$100 \times \frac{\text{Test surface } OD_{405}}{\text{Pristine } TiOD_{405}}$$

Cytocompatibility assessment. Cell viability on the different surfaces was determined with an enzymatic driven colorimetric assay, CellTiter 96 Aqueous One (Promega)[61]. The enzyme uses ATP to drive enzyme function, so only live cells convert the substrate into the compound that is detectable in the spectrophotometer. The viability of osteoblast cells was determined on surfaces including Ti, LN-Ti, Ti coated with $Ag^+$ (Ti—$Ag^+$), LN—Ti—$Ag^+$, and LN-Ti/LI-Ag. Before seeding osteoblast cells, the test surfaces were preconditioned in DMEM/F-12 media with 10% FBS at 37° C. with 5% carbon dioxide ($CO_2$) for 24 h. At the end of the incubation time, preconditioned test surfaces were transferred to 24 well plates and seeded with suspensions of 40,000 cells/2 mL media Gibco. Osteoblast cells were suspended in DMEM/F-12 media with 10% FBS and 1% Pen/Strep and cultured as reported in the cellular mineralization study section. Test surfaces seeded with osteoblast cells were cultured in a humidified incubator supplemented with 5% $CO_2$ at 37° C. for 24 h. Test surfaces with cells were transferred to a new well and covered with MTT reagent. The reagent to media ratio was 20:100 µL for a total of 360 µL to cover the samples and was allowed to reduce the substrate for 1 h. Next, two aliquots of 100 µL were collected from each test condition and transferred to a 96 well plate and their optical absorbance was recorded at a fixed wavelength of 490 nm using a spectrophotometer, VersaMax (MolecularDevices), which was calibrated with a blank MTT reagent.

Antimicrobial study. The effects of aging and long-term antibacterial properties of Ti, Ti—$Ag^+$, LN-Ti, LN—Ti—$Ag^+$, and LN-Ti/LI-Ag surfaces were assessed by placing each sample in separate 2 ml PBS (Sigma Aldrich) containers. At varying time points (0, 48, 72, and 144 h), the test samples were removed from the PBS solution and the antibacterial activity of the surface was determined by contact killing analysis against gram-positive *Staphylococcus aureus* ATCC 25923 (*S. aureus*) and gram-negative *Escherichia coli* ATCC 25922 (*E. coli*). After each round of antibacterial study, the test samples were placed back in 2 mL of fresh PBS solution. Before conducting each antibacterial study, the samples were cleaned by dipping them in isopropanol (IPA) and drying it in a laminar airflow nitrogen box chamber. Next, 50 µL of 5 $\log_{10}$ $CFU/cm^2$ bacterial suspension in TSB was placed on each test surface. The samples were housed in a 24 well cell culture plate and incubated at 37° C. for 24 h. After the incubation period, a 10 µL of PBS supplemented with 0.1% Tween-20 (Sigma-Aldrich) was added onto the surface of the samples and aspirated to detach the bacteria from the surfaces. Next, 20 µL of the bacterial suspension was withdrawn from the sample surface followed by serial dilution and plated onto the TSB agar plates. The plates were then incubated at 37° C. for 16 h and counting of the active colony-forming units (CFU) was performed. All the experiments were done in triplicates to get the average $\log_{10}$ $CFU/cm^2$.

Furthermore, the extent of the bacterial cell damage caused by LN-Ti/LI-Ag was also determined by the LIVE/DEAD BacLight kit (Thermofisher) on *E. coli* as a representative bacterial strain. For this test, 50 µL of 5 $\log_{10}$ $CFU/cm^2$ bacterial suspension was placed onto the newly prepared LN-Ti/LI-Ag and pristine Ti sample and incubated at 37° C. for 24 h. After the incubation time, the bacterial samples from each surface were recovered by using the aforementioned procedure and stained according to the manufacturer's protocol[13]. In this process, equal volumes of SYTO 9 and propidium iodide were combined and 0.3 µL of dye mixture and added to the 100 µL bacterial suspensions. The samples were mixed thoroughly and incubated at room temperature for 15 min in the dark. The bacterial cells were then imaged by an inverted epi-fluorescence microscope (Nikon Eclipse TS2 Olympus, Waltham, MA) equipped with a camera (photometric cool snap dyno) under a 40× objective and 10× optical lens using a NIS-Elements D software.

Results According to Various Experimentation

Figure 3:
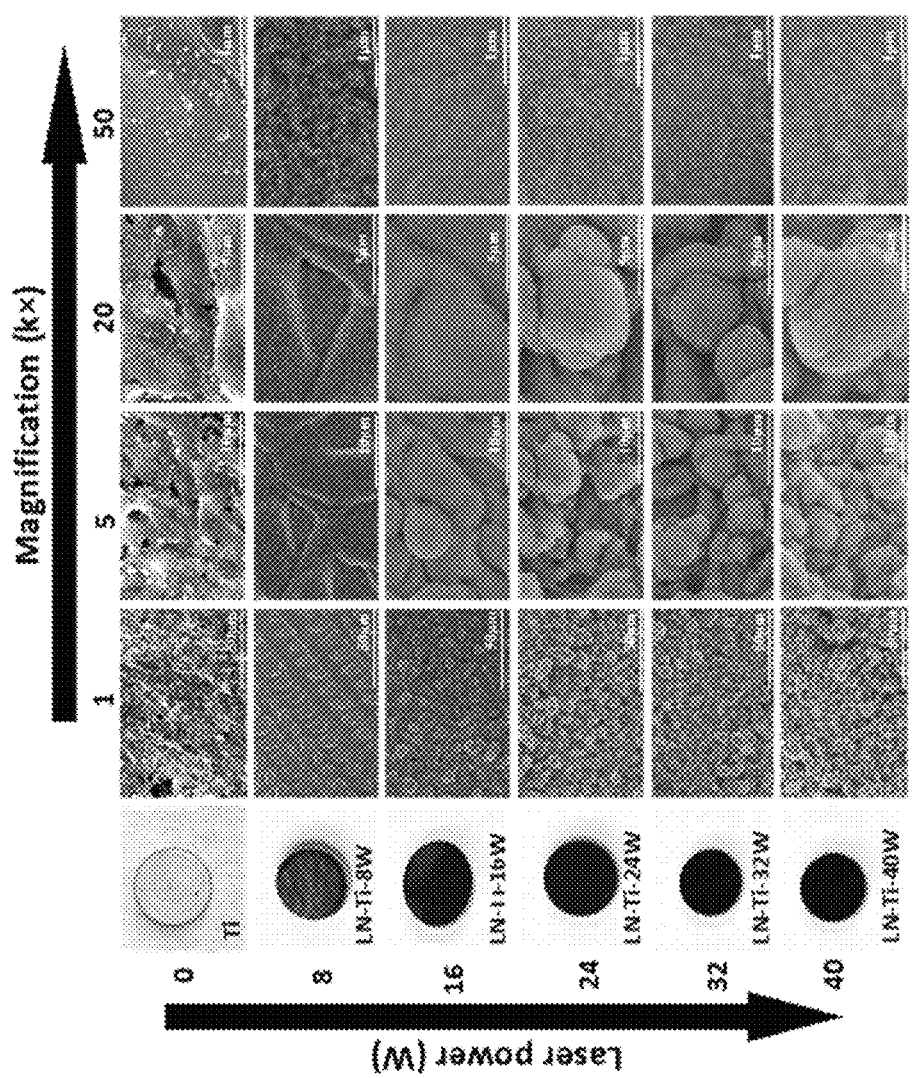
FIG. 3 illustrates morphological analysis of laser nanotextured titanium surfaces (LN-Ti) with varying laser processing power

FIG. 3 illustrates morphological analysis of laser nanotextured titanium surfaces (LN-Ti) with varying laser processing power. FE-SEM images from low to higher magnification (1, 5, 10, and 50 kx) revealed the details of created hierarchical micro and nanostructures on Ti surface by varying laser processing power (8, 16, 24, 32, and 40W).

Laser nanotexturing. Optical images of LN-Ti revealed significant changes in the appearance between Ti and LN-Ti at different laser processing powers (0, 8, 16, 24, 32, and 40 W). The dark color on LN-Ti at higher laser powers (>24 W) is attributed to the laser-induced nanotexture and the graded oxide layer on the Ti surface[13, 62-63]. FE-SEM images were used to evaluate the changes in the hierarchical micro and nanostructures on the Ti surface by varying laser powers. Laser power has a considerable impact on the growth of the oxide layer developed on LN-Ti, FIG. 3. Visually no significant difference in the texture and color was observed in LN-Ti surface that were processed at high laser power settings above 24 W.

Based on the SEM images, pristine Ti surfaces did not show any significant nano or micro roughness; however, after laser processing microstructures and nanostructures of different scales depending on the laser power setting were introduced onto the surface. One common feature among all LN-Ti surfaces with different laser operation powers was the presence of fine nanostructured fuzz that uniformly cover the laser processed Ti samples which was clearly visible at high magnification (50 kx). The impact of laser power pronounced on the micro-scale structures on the processed samples was observed at lower magnification (1, 5, and 10 kx). As shown in FIG. 3, LN surfaces with 8 W processing powers (LN—Ti—8W) showed only a slight deformation on the Ti surface with the formation of shallow (~30 μm) wide trenches which was close to the beam diameter used in the LN process. However, with increasing laser power, different surface structures were emerged on the Ti surface. Higher laser power processed samples (>16 W) showed a more uniform formation of hierarchical micro/nano-topography with round protrusions of grooves in the micrometer regime that were uniformly covered with a fuzz-like nanostructure. The overall size of the fuzz-like nanostructures was similar in size and conformally covered on all LN-Ti samples. Although the average size of the microstructures decreased and porosity increased with the laser processing power, this change wasn't significant in samples that were processed with laser powers above 24 W. Overall, the LN-Ti surfaces with laser processed powers of 24, 32, and 40 W had approximately 4 μm and 1.1 μm microstructures and pores, respectively. Based on these observations, LN-Ti with 32 W laser processing (LN-Ti-32W) was selected for further silver immobilization using the aforementioned laser immobilization process that was described in the experimental section.

Figure 4:
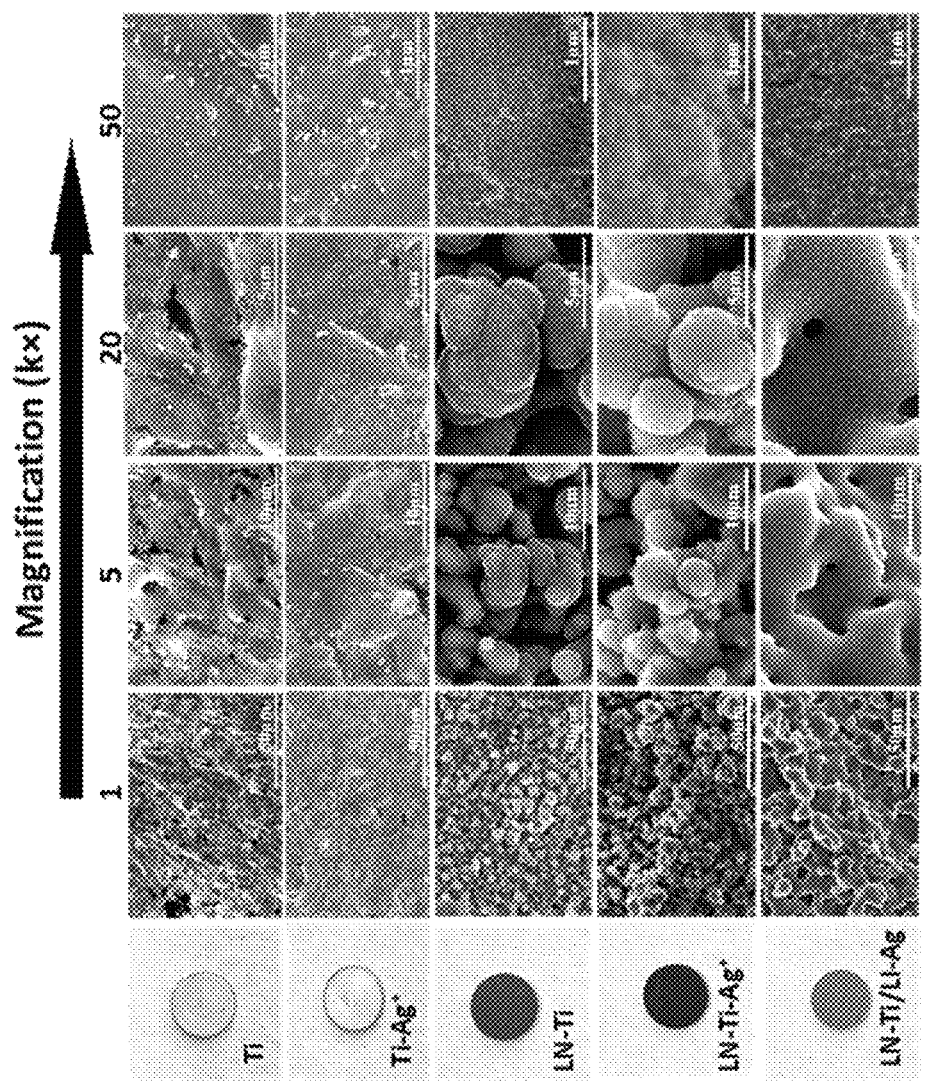
FIG. 4 illustrates a comparison of different surfaces before and after functionalization with silver.

Silver immobilization. FIG. 4 illustrates a comparison of different surfaces before and after functionalization with silver. Optical photograph and SEM image are provided at different magnifications (1, 5, 10, and 50 kx) of Ti, Ti-Ag+, LN-Ti, LN—Ti-Ag+, and LN-Ti/LI-Ag. From the optical images, no noticeable changes were observed before and after treating the pristine Ti with the ionic silver solution (Ti-Ag+). However, LN-Ti shows a slight color change from black to light grey after the treatment with an ionic silver solution (LN—Ti—Ag$^+$) and to light brown after the lower power laser immobilization (LN-Ti/LI-Ag), which is the typical color of AgNPs[64]. Further, the FE-SEM images verified the same; the treatment with ionic silver solution did not cause any noticeable change in morphology of pristine Ti and LN-Ti surfaces. However, after the low-power laser surface treatment, the bead-like structures found in LN—Ti—Ag$^+$ were fused, forming highly microporous plate-like structures while maintaining a uniform fuzz-like nanostructure on its surface. The SEM images of LN-TI/LI-Ag confirmed that the second low-power laser process allows a simultaneous reduction and immobilization of AgNPs into the LN-Ti surface, creating a highly porous Ti—Ag alloy[65]. EDX analysis was conducted to determine the elemental composition of Ti, Ti—Ag$^+$, LN-Ti, LN—Ti—Ag$^+$, and LN-Ti/LI-Ag.

Figure 5:
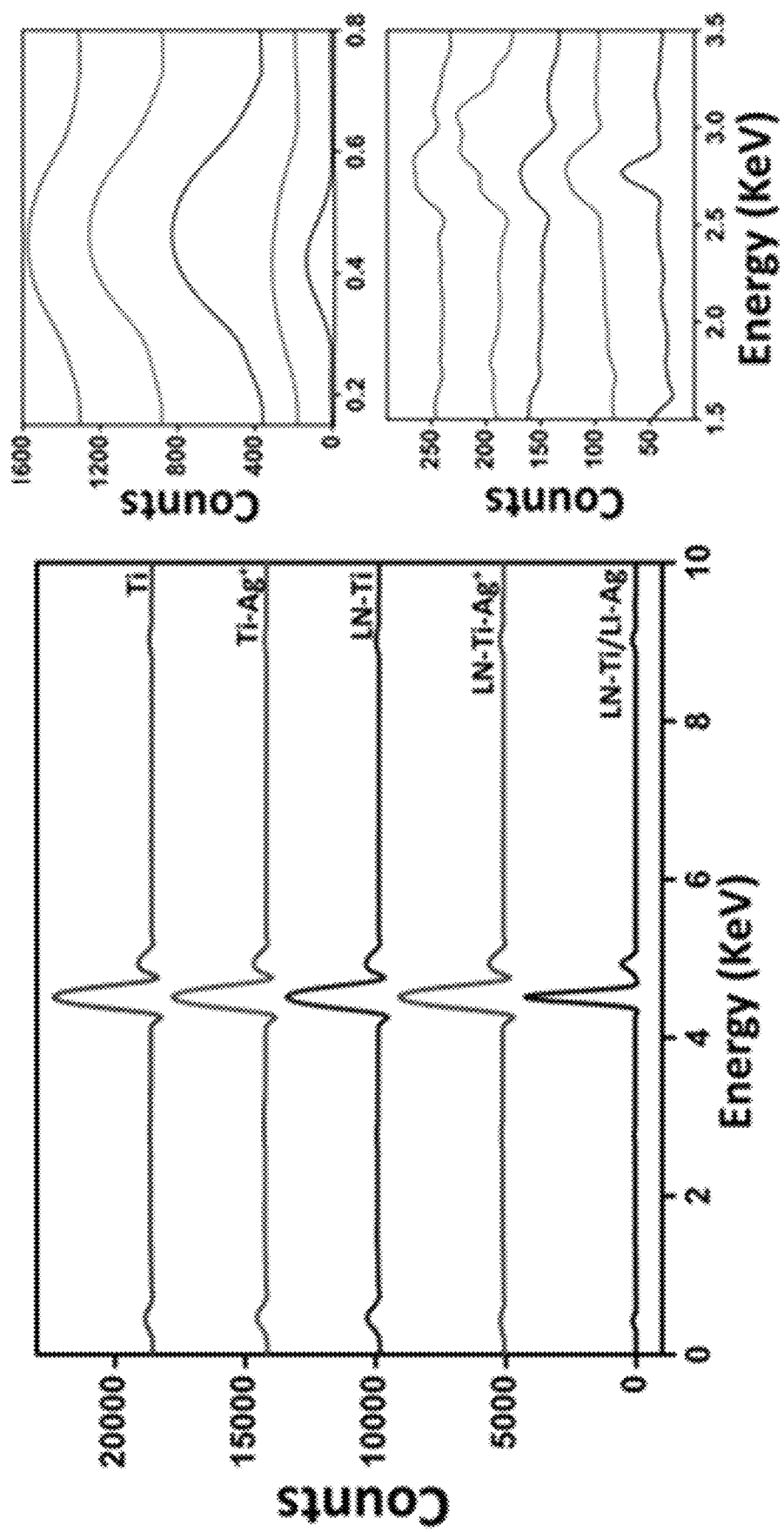
FIG. 5 illustrates energy-dispersive X-ray spectroscopy (EDX) spectrum analysis of titanium Ti, Ti—$Ag^+$, LN-Ti, LN—Ti—$Ag^+$, and LN-Ti/LI-Ag. with zoomed in peaks revealing the presence of Ag in Ti—$Ag^+$, LN—Ti—$Ag^+$, and LN-Ti/LI-Ag.

FIG. 5 illustrates EDX spectrum analysis of titanium Ti, Ti—Ag$^+$, LN-Ti, LN—Ti—Ag$^+$, and LN-Ti/LI-Ag. with zoomed in peaks revealing the presence of Ag in Ti—Ag$^+$, LN—Ti—Ag$^+$, and LN-Ti/LI-Ag. From the EDX spectrum, it was observed that all the samples had common peaks for the following elements Titanium (Ti), Oxygen (O), and Carbon (C). However, laser textured surfaces (LN-Ti, LN—Ti—Ag$^+$, and LN-Ti/LI-Ag) showed a clear O peak with higher intensity than non-textured surfaces (Ti, and Ti—Ag) which confirmed the higher content of titanium oxide (TiO$_2$) as result of laser processing the Ti surface in atmospheric conditions[66]. Peaks at 3.0, 3.2, and 3.4 keV were observed only with Ti—Ag$^+$, LN—Ti—Ag$^+$, and LN-Ti/LI-Ag, which corresponded to the existing Ag. It is evident from the EDX spectrum that the intensity of Ag peaks was higher with LN—Ti—Ag$^+$ as increased surface area on the LN sample allowed an increased attachment of Ag compounds onto its surface.

Figure 6:
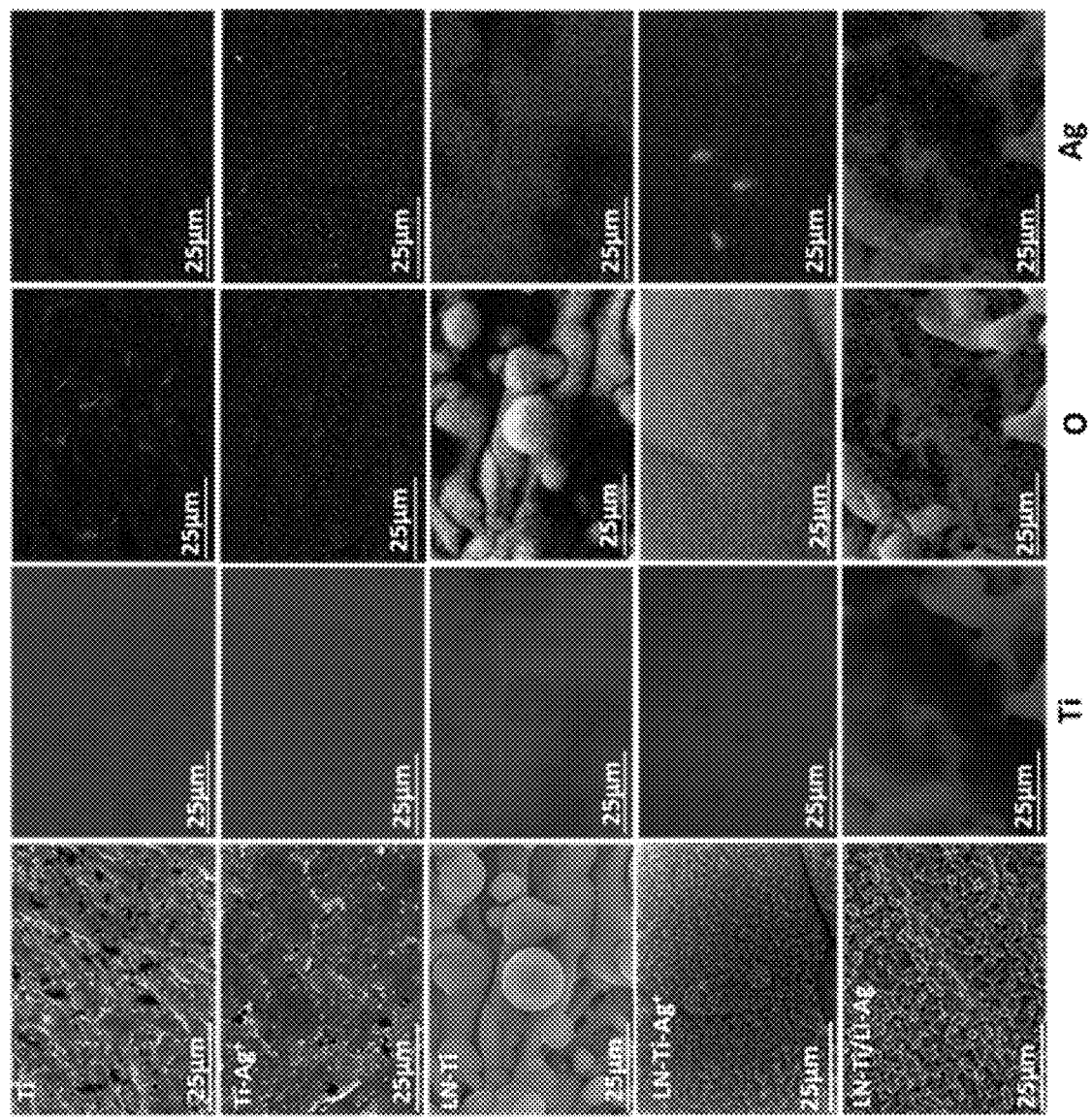
FIG. 6 illustrates EDX elemental mapping of Ti-Titanium (Red), Ag-Silver (Green), and O—Oxygen (yellow) on Ti, Ti—$Ag^+$, LN-Ti, LN—Ti—$Ag^+$, and LN-Ti/LI-Ag surface.

FIG. 6 illustrates EDX elemental mapping of Ti-Titanium (Red), Ag-Silver (Green), and O—Oxygen (yellow) on Ti, Ti—Ag$^+$, LN-Ti, LN—Ti—Ag$^+$, and LN-Ti/LI-Ag surface. To further investigate the distribution of all elements throughout the sample surface, SEM-EDX elemental mapping was performed. The elemental map of LN-Ti had a uniform distribution of yellow-colored dots that showed the homogenous formation of laser-induced oxides (TiO/TiO$_2$) onto the Ti surface. The EDX elemental mapping of LN-Ti—Ag$^+$ and LN-Ti/LI-Ag confirmed the uniform distribution of Ag (green) on both surfaces, further confirming that the LI processor did not affect the uniform distribution of Ag compounds on the LN-Ti—Ag$^+$ surface.

XRD and Raman Spectroscopy. To determine the structural composition and crystallinity of LN-Ti before and after Ag immobilization, XRD and Raman spectroscopy analysis were performed.

Figure 7B:
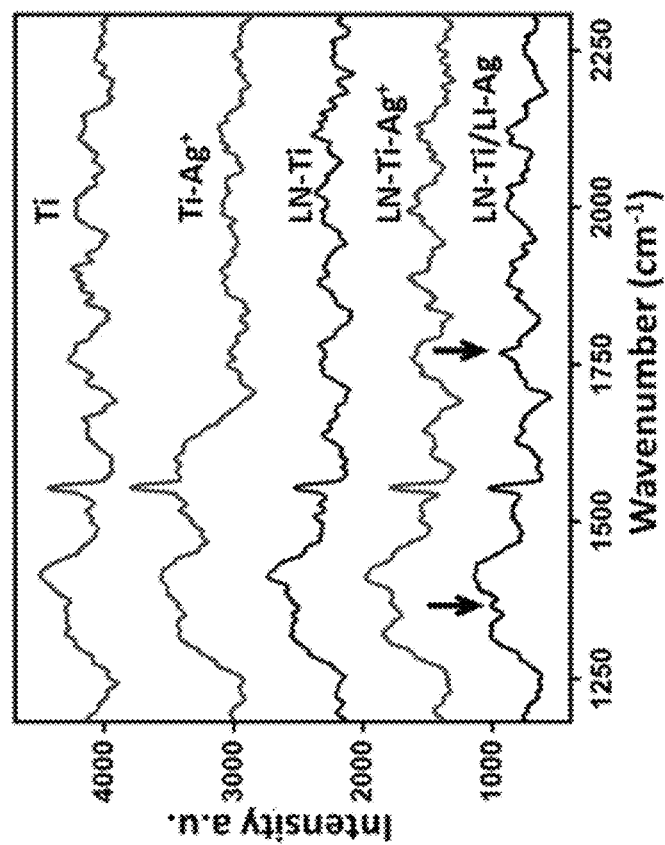
FIG. 7A-B illustrate material characterization of Ti, Ti—$Ag^+$, LN-Ti, LN—Ti—$Ag^+$, and LN-Ti/LI-Ag.
Figure 7A:
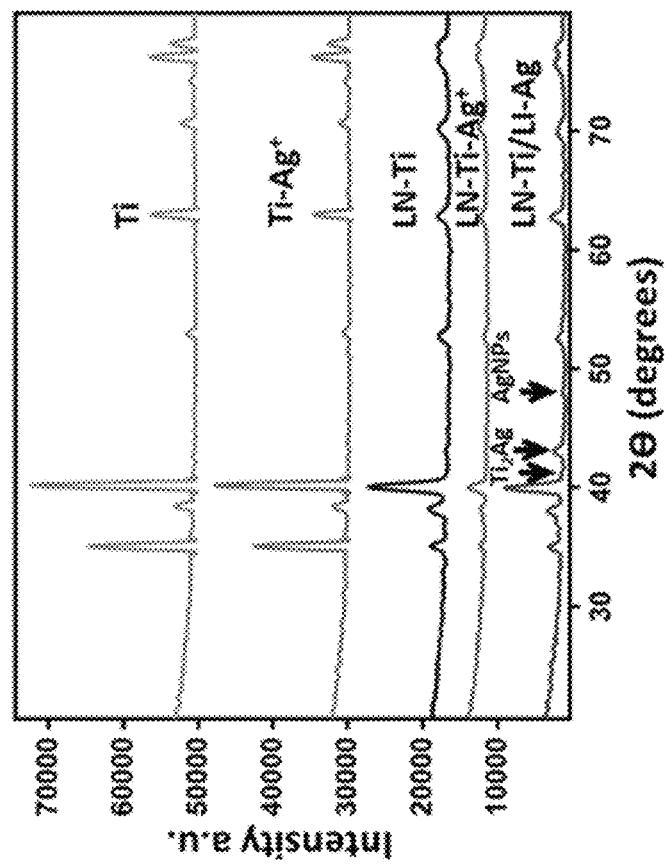

FIG. 7A-B illustrate material characterization of Ti, Ti—Ag$^+$, LN-Ti, LN—Ti—Ag$^+$, and LN-Ti/LI-Ag. FIG. 7A shows XRD and FIG. 7B show Raman Spectroscopy, presence of AgNPs were indicated by arrows confirming photothermal reduction of Ag$^+$ into AgNPs.

FIG. 7A shows the XRD spectrum of Ti, Ti—Ag$^+$, LN-Ti, LN—Ti—Ag$^+$, and LN-Ti/LI-Ag. It can be observed that the XRD pattern of pristine Ti primarily contains eight diffraction peaks (JCPDS No. 44-1294) at 2θ=35°, 37.1°, 41.2°, 52.8°, 64.2°, 71.4°, 76.5° and 77.9° corresponding to the (100), (002), (101), (102), (110), (103), (112) and (201) crystalline planes, respectively[67]. Next, the XRD pattern of Ti—Ag$^+$ demonstrated similar peaks, which indicate the surface treatment with diamminesilver does not change the overall crystalline structure of the material. Further, the XRD spectrum of LN-Ti shows similar peak position with change in intensity and broadening of the peaks. This is associated with a decrease in Ti grain size on the surface of the laser processed samples, which can be explained by the fact that during the laser nano texturing process, the rapid high-temperature ablation and cooling results in a quenched metal surface with smaller grains and Ti/TiO nanostructures[68]. This results in XRD spectra with the same peak locations but broadening of the peaks. Next, the X-ray diffractogram of LN—Ti—Ag$^+$ demonstrates relatively identical pattern and peak positions, which can be explained by the fact that [Ag(NH$_3$)$_2$]$^+$ does not change the overall crystalline properties of the surface[69]. However, after the laser immobilization process (LN-Ti/Li—Ag), a few new peaks were observed. Due to the fact that both Ti and Ag demonstrate almost similar XRD pattern along with the obvious entrapment of Ag into existing rough Ti surface, the presence of Ag was confirmed by two additional diffraction at 2θ=38.8°, 44.5° and an overlapped peak at 2θ=64.2° in the XRD pattern of LN-Ti/LI-Ag samples, indicating the formation of AgNPs and Ti—Ag intermetallic phases, namely TiAg (ICSD card 605934) and/or Ti$_2$Ag (ICSD card 605935) which is in good agreement with the 4-0783 JCPDS card[68, 70, 71]. These results further confirm the simultaneous reduction of [Ag(NH$_3$)$_2$]$^+$ through localized high temperature created by laser, which results in the immobilization of Ag onto the rough Ti surface and formation of intermetallic mixing and Ti—Ag voids at the interface of the laser process samples[72]. Furthermore, some of the Ti, TiO, and Ag peaks are virtually overlapping in the XRD spectrum[73-74]; hence, to get more insight into the elemental composition of the test surfaces, Raman spectroscopy was performed. Raman spectroscopy was carried out to further determine the elemental composition of surfaces and the effect of LN and LI. FIG. 7B shows the Raman spectrum of Ti, Ti—Ag$^+$, LN-Ti, LN—

Ti—Ag⁺, and LN-Ti/LI-Ag. The peaks at 1362 and 1647 cm-1 correspond to AgNPs which is observed only with LN-Ti/LI-Ag confirming the photothermal reduction of Ag⁺ into the form of AgNPs by LI[75].

Water contact angle analysis. Surface wettability has a strong influence on the ability of the implant material towards cellular mineralization. This property is commonly determined by WCA analysis.

Figure 8:
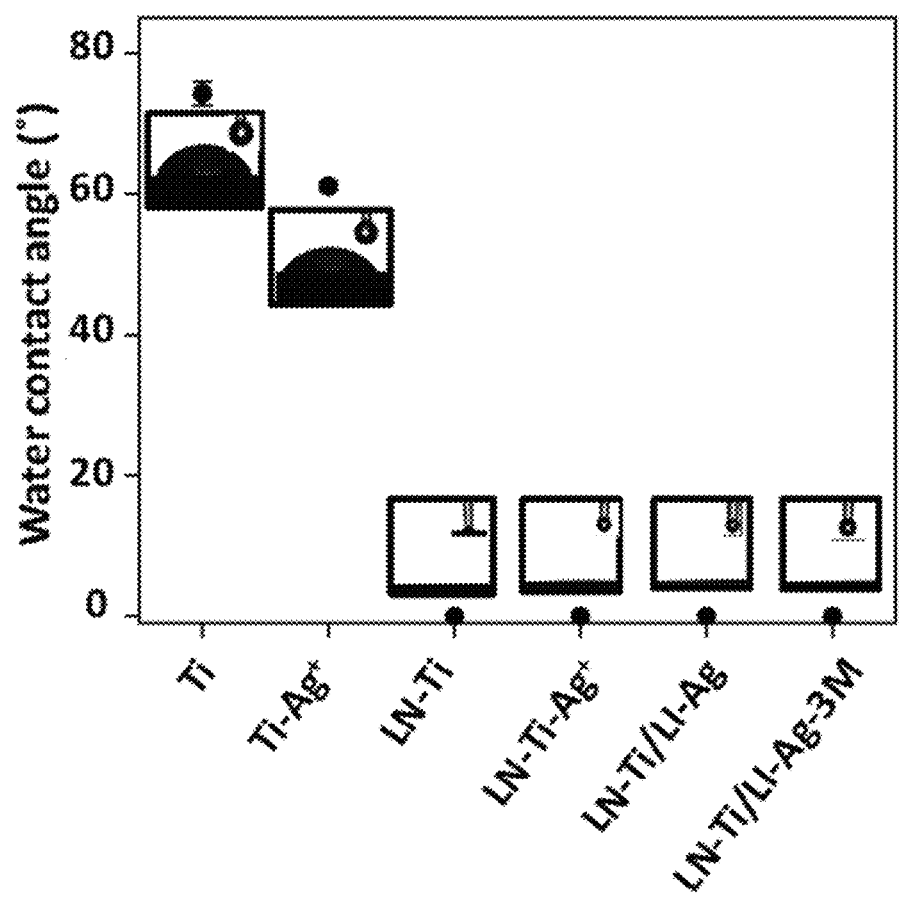
FIG. 8 illustrates water contact angle analysis with a scatter plot showing water contact angle of Ti, Ti—$Ag^+$, LN-Ti, LN—Ti—$Ag^+$, LN-Ti/LI-Ag and LN-Ti/LI-Ag after 3 months storage in ambient conditions (labeled as LN-Ti/LI-Ag-3 m).

FIG. 8 illustrates Water contact angle analysis. Scatter plot showing water contact angle of Ti, Ti—Ag⁺, LN-Ti, LN—Ti—Ag⁺, LN-Ti/LI-Ag and LN-Ti/LI-Ag after 3 months storage in ambient conditions (labeled as LN-Ti/LI-Ag-3 m). Inset images showing the water contact angle of respective samples. FIG. 8 shows a high WCA of ~108° and 0° for samples without laser treatment (Ti, and Ti—Ag⁺) and for all laser processed samples (LN-Ti, LN—Ti—Ag⁺, and LN-Ti/LI-Ag) respectively. While many surface treatments such as corona and plasma treatment last only for few days, results show that the LN-Ti/LI-Ag maintain their high level of hydrophilicity even after 3 months of storage in the ambient (labeled as LN-Ti/LI-Ag-3 m). The observed highly stable super hydrophilic properties are attributed to the generation of highly stable hygroscopic metal oxides[76] in the hierarchical micro and nanostructures on the laser processed Ti surface.

Figure 12:
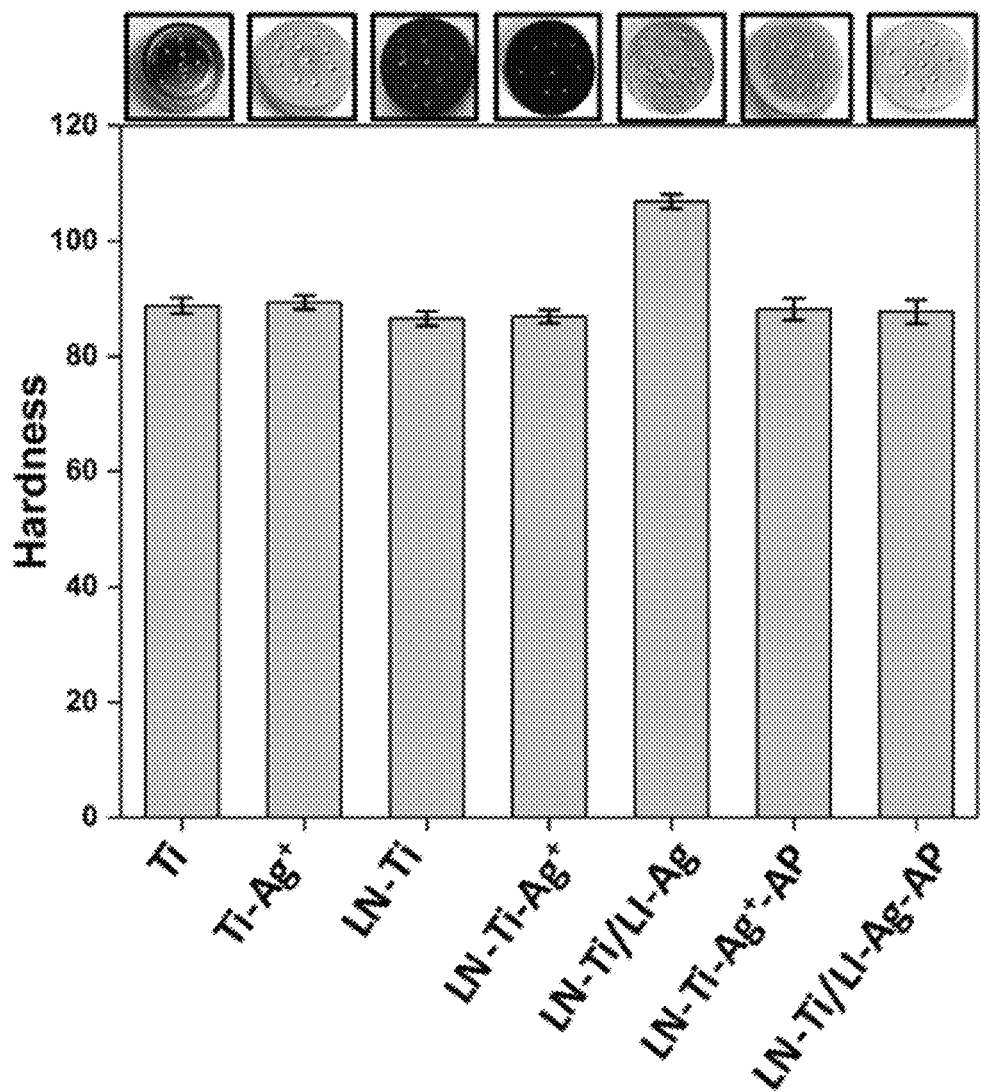
FIG. 12 shows the scale ranges of Rockwell hardness C measurement of pristine Ti, Ti—$Ag^+$, LN-Ti, and LN—Ti—$Ag^+$, and LN-Ti/LI-Ag before and after mechanically polishing (denoted as LN—Ti—$Ag^+$-AP and LN-Ti/LI-Ag-AP).

Rockwell hardness analysis. FIG. 12 shows the scale ranges of Rockwell hardness C measurement of pristine Ti, Ti—Ag⁺, LN-Ti, and LN—Ti—Ag⁺, and LN-Ti/LI-Ag before and after mechanically polishing (denoted as LN—Ti—Ag⁺-AP and LN-Ti/LI-Ag-AP). Based on the measurements, LN-Ti/LI-Ag showed 20.3% higher hardness when compared to pristine Ti. Usually, alloys of Ti—Ag exhibit higher hardness and better scratch-resistant properties when compared to pristine Ti 77. These observations further confirmed the LI of AgNPs onto LN surfaces of Ti and the formation of a Ti—Ag alloy.

Figure 9B:
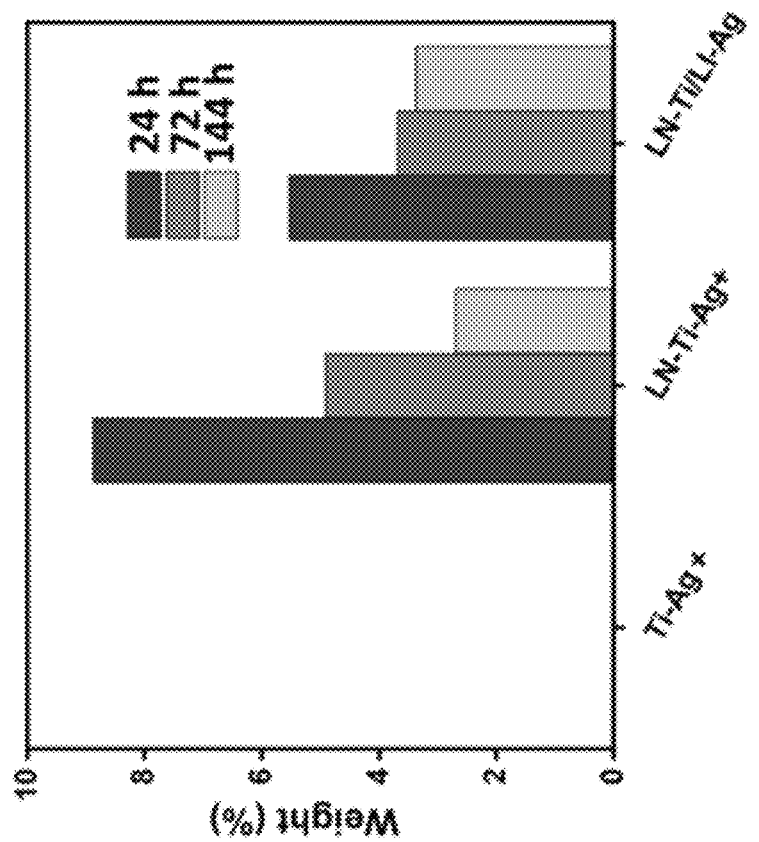
FIG. 9A-C illustrates results from monitoring Silver (Ag) leaching from different surfaces.
Figure 9A:
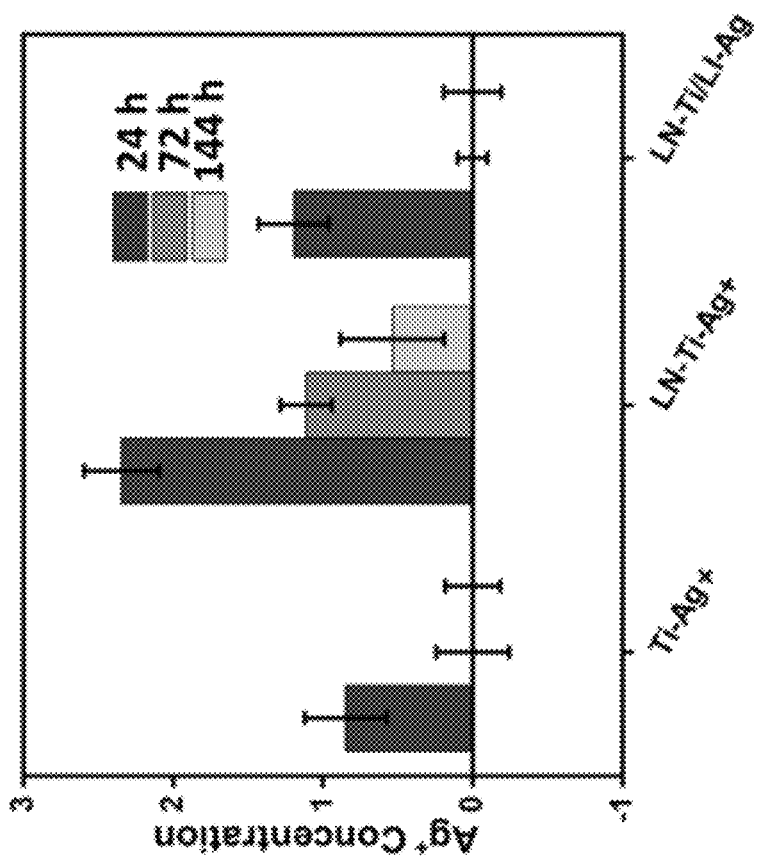
Figure 9C:
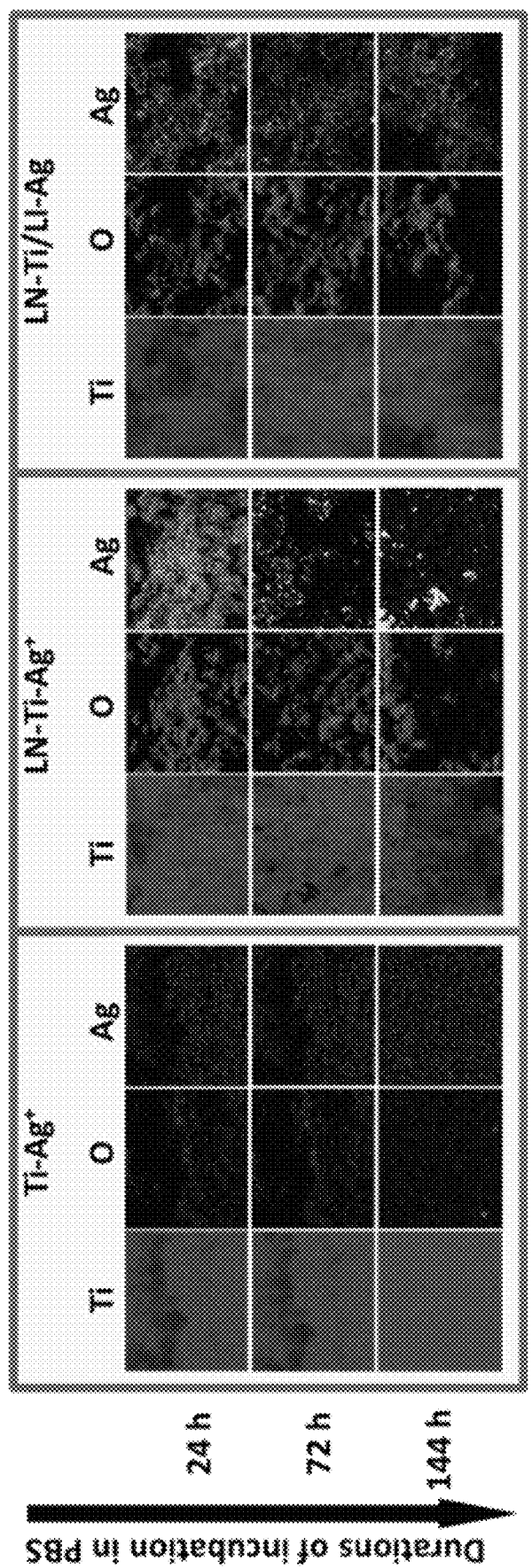

Silver leaching study. FIG. 9A-C illustrates results from monitoring Silver (Ag) leaching from different surfaces. Elemental map of test surfaces Ti—Ag⁺, LN—Ti—Ag⁺, and LN-Ti/LI-Ag after conducting silver leaching study by incubating the surfaces in phosphate buffered saline (PBS) for 24, 72 and 144 h. FIG. 9A illustrates the concentration of Ag leached into the incubation solution (PBS) over time. FIG. 9B illustrates the weight percentages of remaining Ag on different surfaces after different duration of incubation in PBS. FIG. 9C illustrates EDX color mapping of Ti-Titanium (Red), Ag-Silver (Green), and O—Oxygen (yellow), respectively.

To confirm that the LI process has helped in preventing the leaching of Ag from LN-Ti/LI-Ag surface, silver leaching study was performed on Ti—Ag⁺, LN—Ti—Ag⁺ and LN-Ti/LI-Ag test surfaces. In this, all test surfaces were incubated in phosphate buffered saline (PBS) at 37° C. for 24, 72, and 144 h. The amount of Ag leached into the incubation solution (PBS) at the given time interval was monitored by potentiometric titration method using a Silver Ion-Selective Electrode (ISE) in tandem with an auto-titrator system (FIG. 9A). It can be observed that the test surface Ti—Ag⁺ exhibits a rapid burst of initial release and decreases overtime. This can be explained by the fact that the overall effective surface on the pristine titanium is lower as compared to the laser-processed surfaces. Since the silver is not immobilized it can quickly release into the environment. Further, these results can also be explained by the EDX mapping (FIG. 9B), which shows that a very rare amount of silver is present on the test surface after an incubation of 24 h. Also, no significant change in the presence of silver was observed after increasing the incubation time to 48 h and 144 h, indicating the burst release of silver during 24 h incubation time, which is in good agreement with the previous results shown in (FIG. 9A). Next, the LN—Ti—Ag⁺ surface shows (FIG. 9B) the higher release as compared to the other surfaces, which can be explained by the high surface area created during the laser texturing process. It has a sustained release over time which can be explained by the fact that it's not immobilized and gradually released into the environment. This observation can also be supported by the EDX mapping (FIG. 9C), which is clearly showing that some remnants of silver are present on the surface at different time points of incubation. Further, the LN-Ti/LI-Ag surface showed (FIG. 9A) some release at the beginning but rapidly decreased over time which further confirmed that the silver was strongly immobilized onto the surface.

TABLE 1

Surface elemental weight percentage analysis of Ti—Ag⁺, LN-Ti—Ag⁺, and LN-Ti/LI-Ag after different durations of incubation in PBS.

| Ele- | Ti—Ag⁺ (Wt %) | | | LN-Ti—Ag⁺ (Wt %) | | | LN-Ti/LI-Ag (Wt %) | | |
| --- | --- | --- | --- | --- | --- | --- | --- | --- | --- |
| ments | 24 h | 72 h | 144 h | 24 h | 72 h | 144 h | 24 h | 72 h | 144 h |
| O | 2.53 | 9.46 | 0 | 26.11 | 24.54 | 27.87 | 21.74 | 23.06 | 20.57 |
| Ti | 95.67 | 88.31 | 89 | 62.74 | 67.36 | 66.91 | 71.66 | 72.22 | 74.83 |
| Ag | 0.01 | 10 | 0 | 8.87 | 4.91 | 2.69 | 5.53 | 3.69 | 3.38 |

Interestingly, the EDX mapping also supported this observation by showing the presence of silver on its surface even after 144 h incubation. To be more quantitative, FIG. 9B and Table 1 show the weight percentage (determined by EDX analysis) of Ag present on the test surfaces after different durations of incubation in PBS. The weight percentage analysis demonstrates that 0.01, 0, and 0 wt % (Ti—Ag⁺), 8.87, 4.91, and 2.69 wt % (LN—Ti—Ag⁺) and 5.53, 3.69, and 3.38 wt % (LN-Ti/LI-Ag) Ag was present after 24, 72 and 144 h PBS incubation, respectively, which is in good agreement with silver leaching results. Hence, these results ascertain that LI process significantly helped in immobilizing Ag into the nano porous lattices of the LN-Ti and its leaching into the environment.

Bone cell mineralization. An in vitro bone cell mineralization was performed to determine the interaction of cells on different laser-processed surfaces. The process included the differentiation of osteoblasts from MSCs in vitro to form a calcified extracellular matrix on the surfaces. Thus, quantifying the amount of calcium deposited into the extracellular matrix can effectively demonstrate the osteoinductive capability of a surface. In this study, MSCs were utilized to assess the biomineralization ability of LN-Ti-(0, 8, 16, 24, 32 and 40 W) surfaces. Though there are many mice and human cell lines available, the physiology and phenotype of cells that orthopedic devices will encounter upon implantation are better reflected by primary human cells. As cell selection is important for the experimental outcome. Osteoblasts are commonly used as they are in a pre-differentiated proliferative state that virtually guarantees some amount of mineralization. However, in vivo proliferating MSCs are the primary cells that first encounter a surface implanted into bone. Usually, MSCs need to undergo osteogenic induction by the exposed surface or factors introduced into the culture media. However, in this study, osteogenic induction factors were eliminated from the culture media to demonstrate the osteo-inductive properties imposed by LN-Ti surfaces. In this test LN-Ti-(0, 8, 16, 24, 32, and 40 W) were exposed to 2 ml of MSCs suspension and incubated for 21 days. During the incubation period, MSCs attach onto the surface and differentiate to osteoblast cells which will encourage the deposition of calcium. This process of calcium deposition onto the surface is called mineralization. Degree of mineralization is often considered as an indirect measure to access the osseoinductive capacity of the implant. The level of mineralization is often used as a proxy to determine how well osteointegration will occur between the orthopedic implant and the bone tissue. The level of calcium mineralization onto the surface can be quantified by the staining process. In this, Alizarin red dye binds with inorganic calcium deposits which were used to differentiate the mineralized and unmineralized nodules formed by osteoblast cells.

Figure 10B:
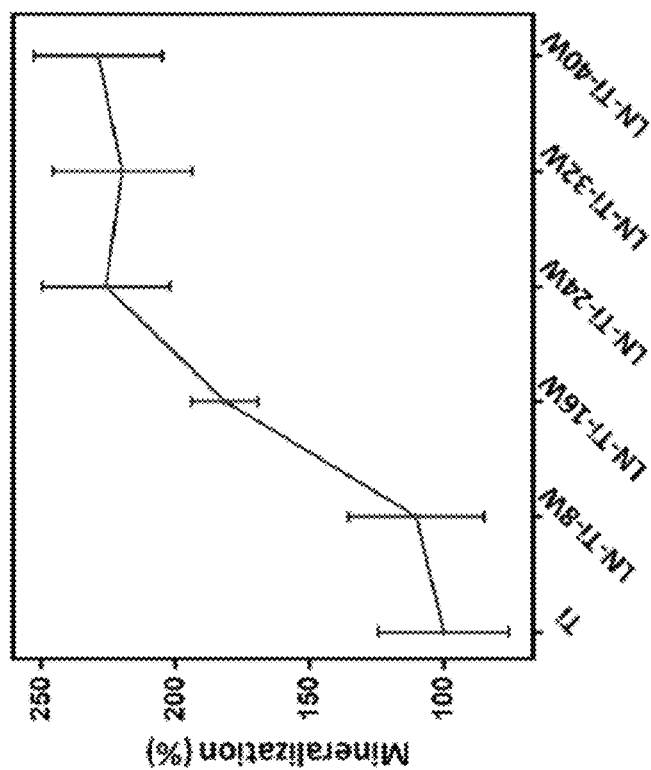
FIG. 10A-D illustrate biomineralization test results on different surfaces.
Figure 10A:
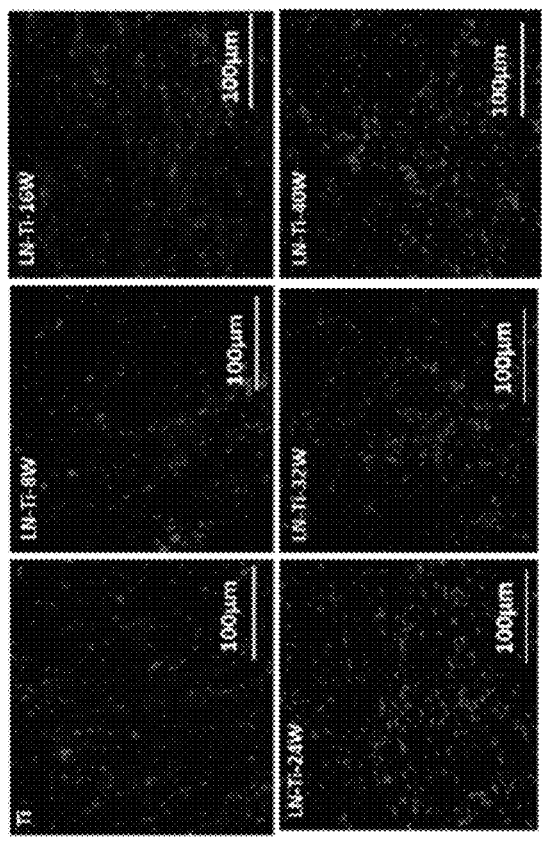
Figure 10D:
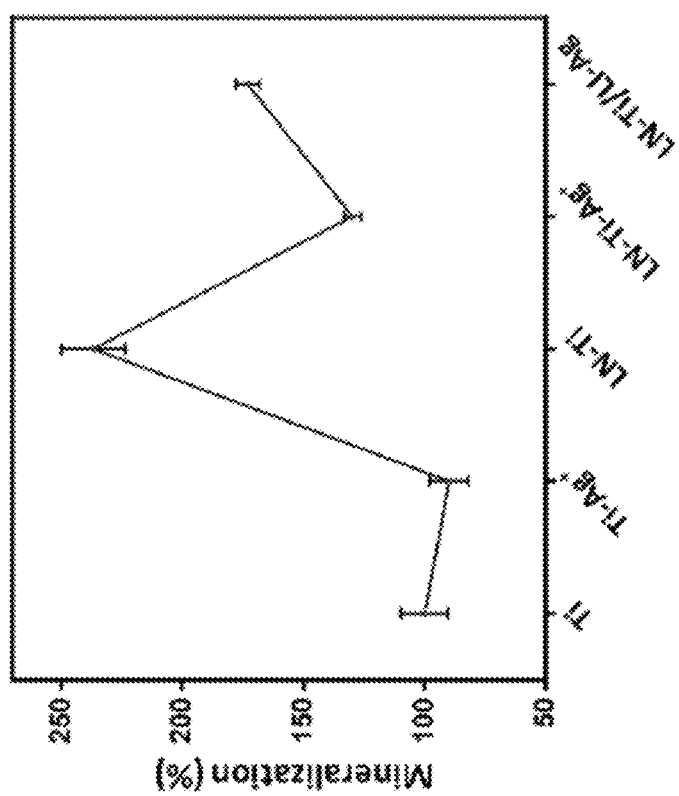

FIG. 10A-D illustrate biomineralization test results on different surfaces. FIG. 10A illustrate microscopic images showing alizarin red-stained osteoblast cells mineralized onto pristine Ti and LN-Ti surfaces fabricated by varying laser processing powers (8, 16, 24, 32, and 40W). FIG. 10B illustrates a plot showing percentage of mineralized cells. FIG. 10O illustrate microscopic images showing alizarin red-stained osteoblast cells mineralized. FIG. 10D illustrates a Plot showing percentage of mineralized cells on Ti, Ti—Ag$^+$, LN-Ti, LN—Ti—Ag$^+$, and LN-Ti/LI-Ag. LN and LI was performed with 30W and 4W, respectively. Cell mineralization percentage was calculated by measuring the absorbance of alizarin red dye eluted from the mineralized surface at OD. Relative change in percentage mineralized cells on different surfaces were calculated with respect to pristine Ti.

FIG. 10A shows microscopic images of alizarin dye-stained LN-Ti-(0, 8, 16, 24, 32, and 40 W). The LN-Ti samples showed a higher degree of mineralization as compared to pristine Ti. The physical roughness created by laser process offered more anchoring sites for cell attachment and mineralization to the surface, which resulted in more distinct staining and red color observed on the surface. The level of cell mineralization onto LN-Ti surfaces was quantified by measuring the absorbance of eluted alizarin stain at OD (FIG. 10B). Based on the recorded absorbance, LN-Ti surfaces showed about 2× higher cellular mineralization properties as compared to pristine Ti. It is well known that surface topography, wettability, and chemical composition has a positive influence on osseointegration[63]. The level of mineralization increased with the increase in laser processing power and saturated after LN-Ti-24W. Among LN-Ti-(24, 32, and 40 W), no significant difference in mineralization properties was observed, as all three surfaces had similar microstructure features which was also confirmed with the aforementioned SEM surface analysis. These results further confirm the appropriate selection of LN-Ti-32W as the optimum surface to implement silver immobilization (LN-Ti/LI-Ag) for added antibacterial properties.

Figure 10C:
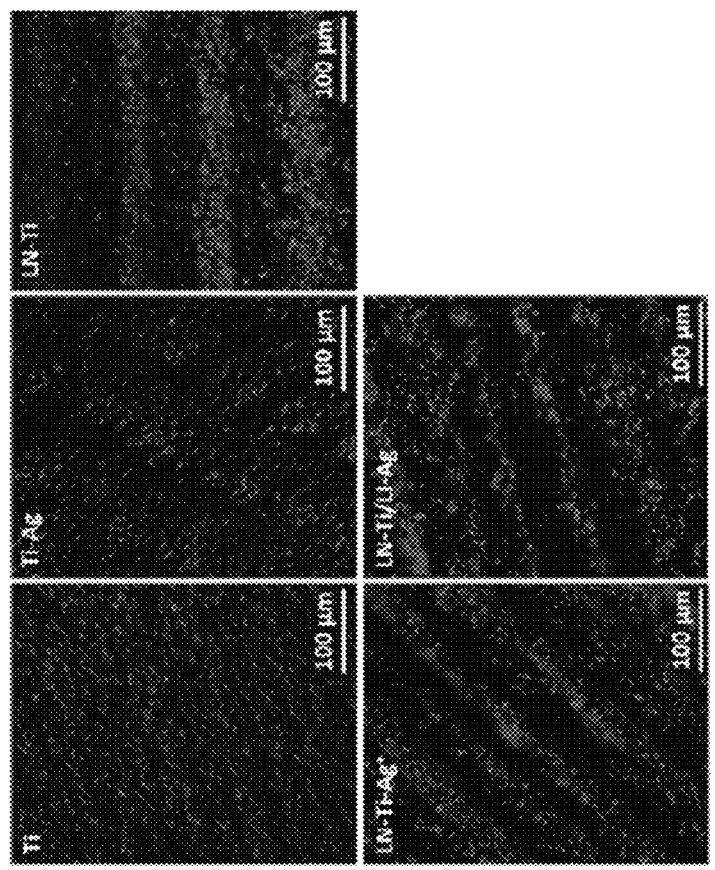

To further assess the potential negative effect of Ag surface functionalization and immobilization on bone cell mineralization, the following surfaces Ti, Ti—Ag$^+$, LN-Ti, LN—Ti—Ag$^+$), and LN-Ti/LI-Ag were compared in terms of the level of bone mineralization using MSCs (FIGS. 10C-D). Quantitative and qualitative evaluation of the mineralization percentage for each surface was determined by alizarin red staining and microscope image. The mineralization percentage of MSCs on Ti, LN—Ti, Ti—Ag$^+$, LN—Ti—Ag$^+$, and LN-Ti/LI-Ag surfaces were found to be 100±9.7, 89.88±8.10, 236.73±13.15, 129.76±3.6 and 173.12±4.97, respectively. Though there was a slight reduction in mineralization percentage of cells on LN-Ti/LI-Ag as compared to LN-Ti it was still 73% higher than Ti. Thus, it can be concluded that the Ag immobilized surface had negligible impact on the cell mineralization and is better than the pristine Ti surface and other Ti surfaces without Ag immobilization (Ti—Ag$^+$ and LN—Ti—Ag$^+$). This observation was also confirmed by biocompatibility studies with MTT assays (See FIG. 13).

Figure 11B:
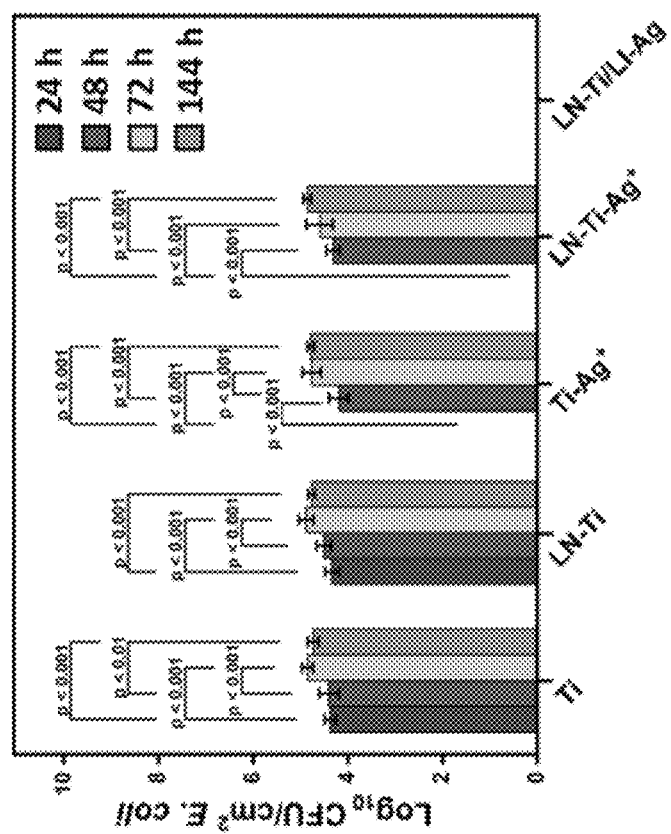
FIG. 11A-B illustrate results from a bactericidal property analysis.
Figure 11A:
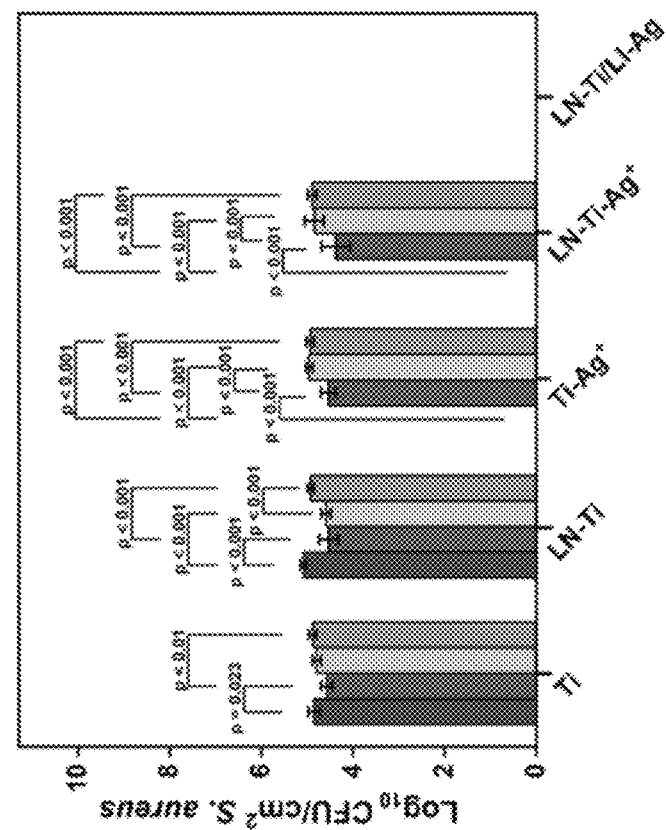

Antimicrobial study. FIG. 11A-B illustrate results from a bactericidal property analysis. Antimicrobial properties of test surfaces including Ti, Ti—Ag$^+$, LN-Ti, LN—Ti—Ag$^+$, and LN-Ti/LI-Ag were analyzed by contact killing method. Number of viable *S. aureus* (FIG. 11A) and *E. coli* (FIG. 11B) on different surfaces after incubating them in PBS for 0, 48, 72 and 144 h.

Bactericidal properties were determined against *E. coli* and *S. aureus* as these are the most common pathogens found in implant-associated infections[80]. The stable antibacterial properties of Ti, Ti—Ag$^+$, LN-Ti, LN—Ti—Ag$^+$, and LN-Ti/LI-Ag were assessed against bacterial suspension containing 4.72 and 5.81 $\log_{10}$ CFU/cm$^2$ of *E. coli* and *S. aureus* suspended in PBS as monoculture (FIGS. 11A and 11B).

As anticipated, Ti and LN-Ti with the lack of any antibacterial silver compounds (AgNPs or Ag$^+$) showed no signs of antibacterial properties as *E. coli* and *S. aureus* survived on both surfaces. Although Ti—Ag$^+$ and LN—Ti—Ag$^+$ surfaces showed high antibacterial properties, they only lasted for 48 h as antibacterial compound (Ag$^+$) gradually leached from these surfaces. In contrast, LN-Ti/LI-Ag surfaces showed a long-lasting antibacterial property against both *E. coli* and *S. aureus* even after 144 h of incubation in PBS (FIG. 14). These results further confirm that the LI allowed the strong attachment of AgNPs into the TiO/TiO$_2$ microstructures of LN-Ti, allowing for long-term and stable bactericidal surface properties. Overall, the LN-Ti/LI-Ag is a super hydrophilic surface functionalized with AgNPs, this super hydrophilic property allows the functionalized surface to establish a closer contact with bacteria and effectively eradicate the bacteria through the contact killing mechanism. Previous studies have shown that AgNPs antibacterial mode of action is through membrane damage and altering transport activity of bacterial cells.[81]. To further validate this effect, the bacterial membrane damage caused through contact with LN-Ti/LI-Ag was analyzed by live/dead assay. For this test, *E. coli* bacterial cultures were suspended in PBS and placed directly onto LN-Ti/LI-Ag and Ti (as control) (See FIG. 14). Although the PBS acts as an isotonic buffer and prevents osmotic shock, however, it does not offer any nutrition for bacterial growth and thus, did not exhibit an increase in the amount of bacteria over time. This method of assessment is often used to test the antibacterial bacterial properties of surfaces through contact killing and the duration that it requires for full eradication[82]. Large number of bacteria cells were stained in green (live) on Ti surface and showed no change in the viability even after 24 h. In the case of LN-Ti/LI-Ag, although most of the bacteria were strained in green (live) with the first contact (0 h), after 24 h all the bacterial cells were stained red (dead) and confirmed cell membrane damage caused by their interaction with silver compounds on the LN-Ti/LI-Ag surface. Overall, despite the use of a two-step laser process for the LN-Ti/LI-Ag surfaces, the developed surface modification process is simple and scalable with better antibacterial and bone cell mineralization properties as compared to many previously reported surface modification technologies, as summarized in Table 2.

improvement in percentage cellular viability. The presence of a denser $TiO_2$ layer on LN has increased the relative permittivity and attachment of the proteins.

TABLE 2

Examples of topographic surface modification on titanium for dual response antibacterial and promote osteogenesis

| Sr. No. | Topographic pattern | Technique | Number of techniques | Biomaterial | Bacteria tested | Antibacterial stability | Ref. |
|---|---|---|---|---|---|---|---|
| 1 | Nano-microphase grain | Compacts and sintered | 2 | ZnO and $TiO_2$ | S. epidermidis | N/A | 8 |
| 2 | Nanowires | Hydrothermal treatment | 1 | $TiO_2$ | P. aeruginosa | N/A | 9 |
| 3 | Sr- and Ag-loaded nanotubes | Anodized titanium, $Sr(OH)_2$ hydrothermal and soaked in $AgNO_3$ | 2 | Titanium foils | S. aureus (MRSA and MSSA) E. coli | N/A | 10 |
| 4 | Zn incorporated nanotubes | Anodization and hydrothermal treatment in Zn-containing solutions | 2 | Titanium | S. aureus | N/A | 11 |
| 5 | Nanotextured surface immobilized with AgNPs | Laser ablation nanotexturing and immobilization of AgNPs | 1 | Titanium | S. aureus and E. coli | 144 hours | This study |

Additional experimentation validation are disclosed herein. FIGS. 12-15 are referenced throughout this detailed description and further described below.

Figure 13:
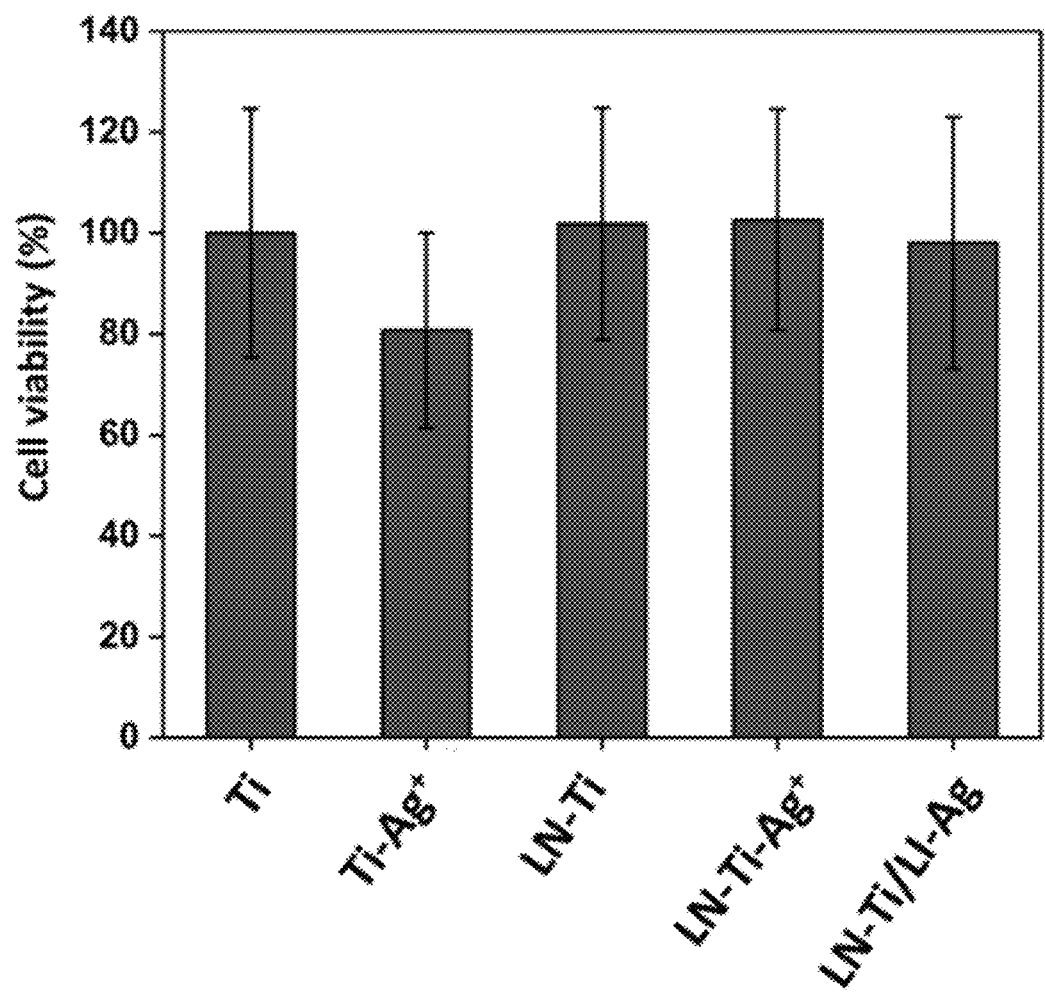
FIG. 13 illustrates results from a cytocompatibility analysis.

FIG. 12 illustrates results from a rockwell hardness analysis. Bar graph showing the hardness of the Ti, Ti—$Ag^+$, LN-Ti, LN—Ti—$Ag^+$, and LN-Ti/LI-Ag. The LN-Ti/LI-Ag after polishing was labeled as LN-Ti/LI-Ag-AP. Optical images of the respective samples are included as an inset above the bar graph FIG. 13 illustrates results from a cytocompatibility analysis. Invitro MTT assay was carried to determine cytocompatibility of Ti, Ti—$Ag^+$, LN-Ti, LN—Ti—$Ag^+$, and LN-Ti/LI-Ag. The viability of mesenchymal stem cells (MSCs) cultured on preconditioned samples was measured by enzymatically driven MTT assay. The viability of cells attached to the test surfaces was measured by reading the absorbance of the MTT reagent and converted to percentage viability considered absorbance of Ti as 100%.

Figures 14A, 14B:
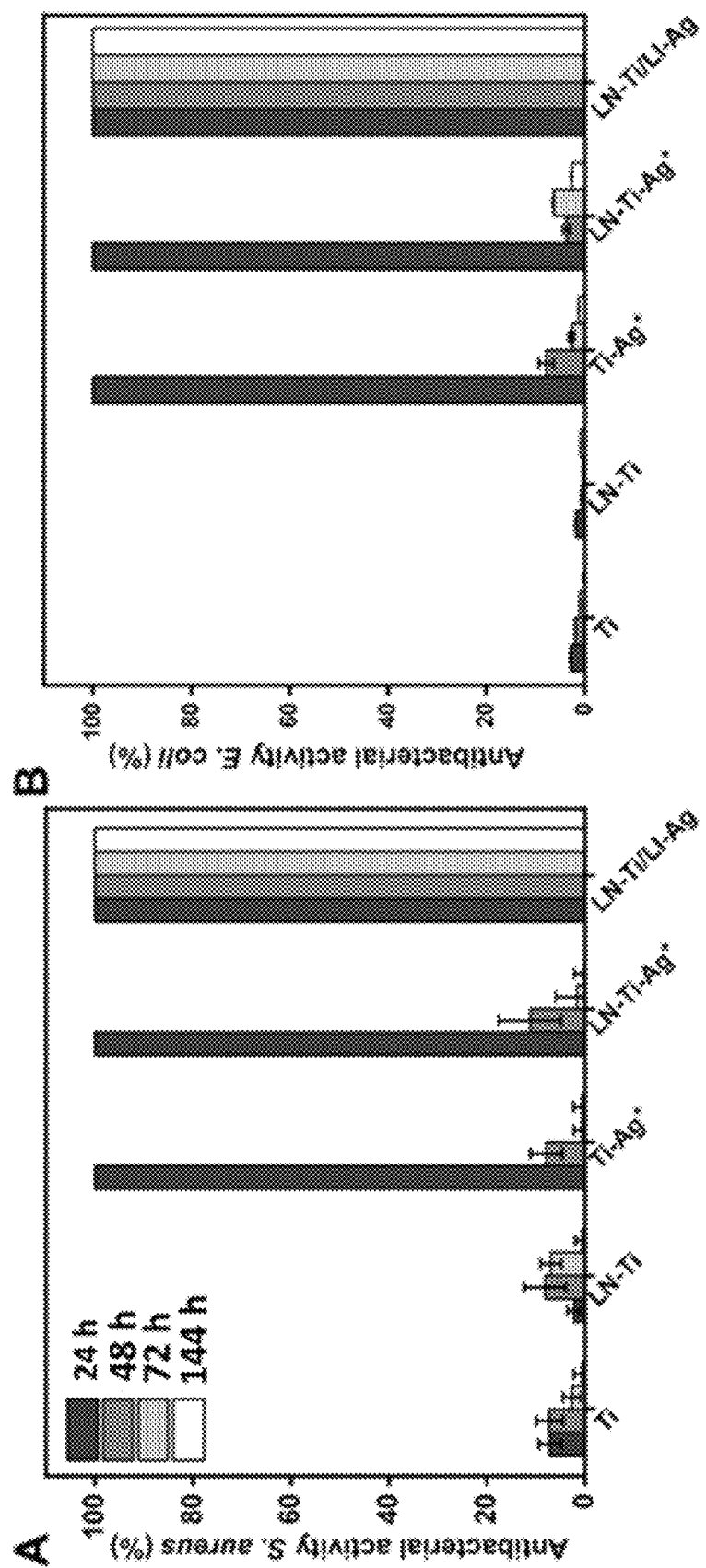
FIG. 14A-B illustrates results from antibacterial activity analysis of different laser processed surfaces against *S. aureus* and *E. coli* after continues incubation in PBS for 0, 48, 72 and 144 hours.

Cytocompatibility is an important characteristic of a successful implant. Earlier studies have reported the cytotoxic and genotoxic response of Ag and $TiO_2$ particles to mammalian cells. Hence, it is essential to assess the cytocompatibility of the material developed in this study. An in vitro MTT assay was performed to evaluate the viability of MSCs (normalized against the control group) cultured on Ti, Ti—$Ag^+$, LN-Ti, LN—Ti—$Ag^+$, and LN-Ti/LI-Ag after preconditioning the samples in DMEM for 24 h, Figure S2. The preconditioning was performed to mimic the in vivo environment. In a host, blood rushes to the implant site, and blood proteins are adsorbed to the surface. The degree of protein adsorption is affected by the physical and chemical properties of the implant material. No significant cytotoxic response was observed among all five samples. This helped us to confirm that the hierarchical nanotextures induced by laser irradiation offered an increase in protein adsorption in the preconditioning step, this biological stimulus aided an FIG. 14A-B illustrates results from antibacterial activity analysis of different laser processed surfaces against S. aureus (FIG. 14A) and E. coli (FIG. 14B) after continues incubation in PBS for 0, 48, 72 and 144 hours. The antibacterial activity at different time points was calculated as (Initial CFU−Final CFU)/Initial CFU×100.

Figure 15:
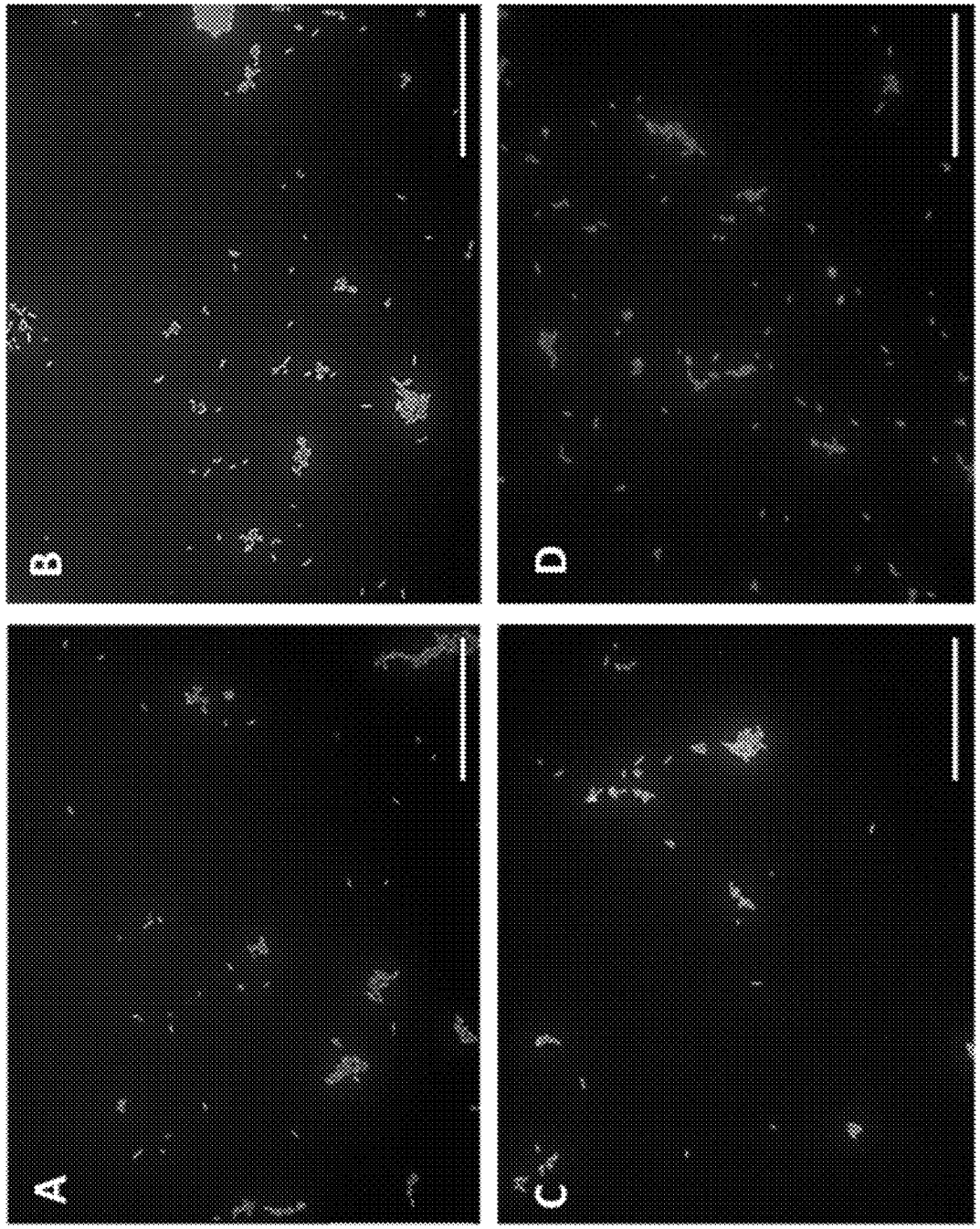
FIG. 15 illustrates viability of *E. coli* after exposure to Ti and LN-Ti/LI-Ag surfaces for 0 and 24 h using live/dead differential staining.

FIG. 15 illustrates viability of E. coli after exposure to Ti and LN-Ti/LI-Ag surfaces for 0 and 24 h using live/dead differential staining. Epi-fluorescent images of E. coli exposed to A) Ti (0 h), B) Ti (24 h) C) LN-Ti/LI-Ag (0 h), and D) LN-Ti/LI-Ag (24 h), respectively. Bacterial cells in red are indicative of dead bacteria with damaged membrane, while the green indicates live/healthy bacterial cells respectively. The objective was 40×, and all scale bars are 50 μm.

While various embodiments have been described, it will be apparent to those of ordinary skill in the art that many more embodiments and implementations are possible. Accordingly, the embodiments described herein are examples, not the only possible embodiments and implementations.

A second action may be said to be "in response to" a first action independent of whether the second action results directly or indirectly from the first action. The second action may occur at a substantially later time than the first action and still be in response to the first action. Similarly, the second action may be said to be in response to the first action even if intervening actions take place between the first action and the second action, and even if one or more of the intervening actions directly cause the second action to be performed. For example, a second action may be in response to a first action if the first action sets a flag and a third action later initiates the second action whenever the flag is set.

To clarify the use of and to hereby provide notice to the public, the phrases "at least one of <A>, <B>, . . . and <N>" or "at least one of <A>, <B>, <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed.

The invention claimed is:

1. A method, comprising:
    laser nano-texturing a titanium surface of a device configured to be at least partially implanted into a living subject;
    applying an aqueous silver ion solution to form a silver ion complex on the nano-textured titanium surface; and
    reducing, using laser-assisted photocatalytic reduction, the silver ion complex to silver ion particles which are immobilized on the nano-textured titanium surface.

2. The method of claim 1, wherein laser nano-texturing the titanium surface further comprises:
    directing a laser at the surface and forming hierarchical porous structures on the titanium surface.

3. The method of claim 1, wherein reducing, using laser-assisted photocatalytic reduction, the silver ion complex to silver ion particles immobilized on the nano-texturing surface further comprises:
    directing a laser at the silver ion complexes on the nano-textured titanium surface to form the immobilized silver ion particles.

4. The method of claim 1, where in the laser nanotexturing occurs is performed at a first power and the laser-assisted photocatalytic reduction is performed at a second power, wherein the first power is greater than the second power.

5. The method of claim 4, wherein the laser nanotexturing and the reducing is performed with a same laser.

6. The method of claim 1, wherein the silver ion complex comprises $[Ag(NH_3)_2]^+$.

7. The method of claim 1, wherein the device is an orthopedic device and the surface is configured to receive or adjoin a bone.

* * * * *